US009469684B2

(12) United States Patent
Finn et al.

(10) Patent No.: US 9,469,684 B2
(45) Date of Patent: *Oct. 18, 2016

(54) THERAPEUTIC AND DIAGNOSTIC CLONED MHC-UNRESTRICTED RECEPTOR SPECIFIC FOR THE MUC1 TUMOR ASSOCIATED ANTIGEN

(71) Applicants: Olivera J. Finn, Pittsburgh, PA (US); Nehad M. Alajez, Riyadh (SA); Jan Schmielau, Lubeck (DE); Mark D. Alter, Brooklyn, NY (US)

(72) Inventors: Olivera J. Finn, Pittsburgh, PA (US); Nehad M. Alajez, Riyadh (SA); Jan Schmielau, Lubeck (DE); Mark D. Alter, Brooklyn, NY (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 302 days.

This patent is subject to a terminal disclaimer.

(21) Appl. No.: 13/939,988

(22) Filed: Jul. 11, 2013

(65) Prior Publication Data

US 2013/0289261 A1 Oct. 31, 2013

Related U.S. Application Data

(63) Continuation of application No. 12/258,545, filed on Oct. 27, 2008, now abandoned, which is a continuation of application No. 11/295,767, filed on Dec. 7, 2005, now Pat. No. 7,655,461.

(60) Provisional application No. 60/634,072, filed on Dec. 7, 2004.

(51) Int. Cl.
| | |
|---|---|
| *C12N 5/07* | (2010.01) |
| *C07K 14/705* | (2006.01) |
| *C07K 14/725* | (2006.01) |
| *C07K 16/28* | (2006.01) |
| *C07K 16/30* | (2006.01) |
| *A61K 38/00* | (2006.01) |

(52) U.S. Cl.
CPC ..... *C07K 14/70503* (2013.01); *C07K 14/7051* (2013.01); *C07K 16/2809* (2013.01); *C07K 16/3092* (2013.01); *A61K 38/00* (2013.01); *C07K 2317/34* (2013.01); *C12N 2799/027* (2013.01)

(58) Field of Classification Search
None
See application file for complete search history.

(56) References Cited

U.S. PATENT DOCUMENTS

| | | | |
|---|---|---|---|
| 5,424,398 A | 6/1995 | Middeldorp et al. | |
| 5,543,291 A | 8/1996 | Keyomarsi et al. | |
| 5,788,963 A | 8/1998 | Murphy et al. | |
| 5,846,827 A | 12/1998 | Celis et al. | |
| 5,962,318 A | 10/1999 | Rooney et al. | |
| 5,973,119 A | 10/1999 | Coats et al. | |
| 6,225,443 B1 | 5/2001 | DeMars et al. | |
| 6,805,861 B2 | 10/2004 | Stauss | |
| 7,070,995 B2* | 7/2006 | Jensen .................. | C07H 21/04 435/325 |
| 7,704,507 B2 | 4/2010 | Finn et al. | |
| 2002/0090362 A1 | 7/2002 | Stauss | |
| 2002/0150891 A1 | 10/2002 | Hood et al. | |
| 2003/0040617 A9 | 2/2003 | Rosen et al. | |
| 2003/0143647 A1 | 7/2003 | Finn et al. | |
| 2006/0147460 A1 | 7/2006 | Finn et al. | |

FOREIGN PATENT DOCUMENTS

| | | |
|---|---|---|
| WO | WO 96/12406 A1 | 5/1996 |
| WO | WO 98/33450 A1 | 8/1998 |
| WO | WO 99/10379 A1 | 3/1999 |
| WO | WO 99/60119 A2 | 11/1999 |
| WO | WO 00/55351 A1 | 9/2000 |
| WO | WO 03/033520 A2 | 4/2003 |
| WO | WO 2005/113595 A2 | 12/2005 |
| WO | WO 2007/044033 A2 | 4/2007 |
| WO | WO 2010/011994 A2 | 1/2010 |

OTHER PUBLICATIONS

Baxevanis et al, Cancer Immunol Immunother, Oct. 2004;53:893-903.*
Henderikx et al, Cancer Res, 1998, 58:4324-4332.*
Paul, Human Gene Ther, 2000; 11:1417-1428.*
U.S. Appl. No. 60/324,450, filed Sep. 24, 2001, Finn et al.
U.S. Appl. No. 60/634,072, filed Dec. 7, 2004, Finn et al.
U.S. Appl. No. 61/083,800, filed Jul. 25, 2008, Finn et al.
Aarnoudse et al., "TCR Reconstitution in Jurkat Reporter Cells Facilitates the Identification of Novel Tumor Antigens by CDNA Expression Cloning," *Int. J Cancer*, 99(1): 7-13 (May 1, 2002).
Adams et al., "High Affinity Restricts the Localization and Tumor Penetration of Single-Chain Fv Antibody Molecules," *Cancer Res*, 61(12): 4750-4755 (Jun. 15, 2001).
Alajez, "MHC-Unrestricted MUC1-Specific T Cell Receptor for Cancer Immunotherapy/Gene Therapy," Thesis Dissertation, University of Pittsburgh, Dec. 8, 2003.
Alajez et al., "Therapeutic potential of a tumor-specific, MHC-unrestricted T-cell receptor expressed on effector cells of the innate and the adaptive immune system through bone marrow transduction and immune reconstitution," *Blood*, 105(12): 4583-4589 (Jun. 15, 2005).

(Continued)

*Primary Examiner* — Mark Halvorson
(74) *Attorney, Agent, or Firm* — Leydig, Voit & Mayer, Ltd.

(57) ABSTRACT

The invention provides an isolated nucleic acid encoding a receptor, other than an immunoglobulin, wherein the receptor binds to a MUC1 tumor antigen independently of an major histocompatibility complex (MHC). The invention provides a method of activating a signaling pathway and/or killing a cancer cell using a receptor that is similar to or is a T cell receptor.

14 Claims, 15 Drawing Sheets

(56) References Cited

OTHER PUBLICATIONS

Altschul et al., "Basic Local Alignment Search Tool," *J Mol Biol*, 215(3): 403-410 (1990).
Attwood, "The Babel of Bioinformatics," *Science*, 290: 471-473 (Oct. 20, 2000).
Avigan et al., "Immune reconstitution following high-dose chemotherapy with stem cell rescue in patients with advanced breast cancer," *Bone Marrow Transplant*, 26(2): 169-176 (Jul. 2, 2000).
Badou et al., "Mercuric Chloride-Induced Autoimmunity," *Current Protocols in Immunology*, 3(Supplement 32): 15.15.1-15.15.18 (Aug. 1999).
Barany et al., "Solid-phase peptide synthesis: a silver anniversary report," *Int. J. Peptide Protein Res.* 30: 705-739 (1987).
Barnd et al., "Specific, major histocompatibility complex-unrestricted recognition of tumor-associated mucins by human cytotoxic T cells," *Proc Natl Acad Sci U S A,*, 86: 7159-7163 (Sep. 1989).
Barratt-Boyes, "Making the most of mucin: a novel target for immunotherapy," *Cancer Immunology Immunotherapy*, 43(3): 142-151 (1996).
Bensinger et al., "High-dose busulfan, melphalan, thiotepa and peripheral blood stem cell infusion for the treatment of metastatic breast cancer," *Bone Marrow Transplant*, 19(12): 1183-1189 (Jun. 2, 1997).
Berard et al., "Cross-Priming of Naïve CD8 T Cells against Melanoma Antigens Using Dendritic Cells Loaded with Killed Allogeneic Melanoma Cells," *J. Exp. Med.*, 192(11): 1535-1543 (Dec. 4, 2000).
Berkner, "Development of Adenovirus Vectors for the Expression of Heterologous Genes," *Bio Techniques*, 6(7): 616-629 (Jul./Aug. 1988).
Blake et al., "Use of Combinatorial Peptide Libraries to Construct Functional Mimics of Tumor Epitopes Recognized by MHC Class I-Restricted Cytolytic T Lymphocytes," *The Journal of Experimental Medicine*, 184(1): 121-130 (Jul. 1, 1996).
Boël et al., BAGE: a New Gene Encoding an Antigen Recognized on Human Melanomas by Cytolytic T Lymphocytes, *Immunity*, 2: 167-175 (Feb. 1995).
Bozzacco et al., "DEC-205 receptor on dendritic cells mediates presentation of HIV gag protein to CD8+ T cells in a spectrum of human MHC I haplotypes," *Proc. Nat. Acad. Sci. USA*, 104(4): 1289-1294 (Jan. 23, 2007).
Brenner et al., "Gene marking to determine whether autologous marrow infusion restores long-term haemopoiesis in cancer patients," *Lancet*, 342(8880): 1134-1137 (Nov. 6, 1993).
Brichard et al., "The Tyrosinase Gene Codes for an Antigen Recognized by Autologous Cytolytic T Lymphocytes on HLA-A2 Melanomas," *The Journal of Experimental Medicine*, 178(2): 489-495 (Aug. 1, 1993).
Bubenik, "Tumour MHC class I downregulation and immunotherapy (Review)," *Oncology Reports*, 10(6): 2005-2008 (Dec. 2003).
Burchell et al., "A Short Sequence, Within the Amino Acid Tandem Repeat of a Cancer-Associated Mucin, Contains Immunodominant Epitopes," *Int J Cancer*, 44(4): 691-696 (Oct. 15, 1989).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, 111: 2129-2138 (Nov. 1990).
Byun et al., "Analysis of the relative level of gene expression from different retroviral vectors used for gene therapy," *Gene Ther.*, 3(9): 780-789 (Sep. 1996).
Callan et al., "Selection of T cell receptor variable gene-encoded amino acids on the third binding site loop: a factor influencing variable chain selection in a T cell response," *Eur J Immunol*, 25(6): 1529-1534 (Jun. 1995).
Chen et al., "A testicular antigen aberrantly expressed in human cancers detected by autologous antibody screening," *Proc. Natl. Acad. Sci. USA*, 94(5): 1914-1918 (Mar. 4, 1997).
Chung et al., "Functional three-domain single-chain T-cell receptors," *Proc Natl Acad Sci U S A*, 91: 12654-12658 (Dec. 1994).
Clauser et al., "Role of Accurate Mass Measurement (±10 ppm) in Protein Identification Strategies Employing MS or MS/MS and Database Searching," *Analytical Chemistry*, 71(14): 2871-2882 (Jul. 15, 1999).
Coulie et al., "A New Gene Coding for a Differentiation Antigen Recognized by Autologous Cytolytic T Lymphocytes on HLA-A2 Melanomas," *The Journal of Experimental Medicine*, 180(1): 35-42 (Jul. 1, 1994).
Covini et al., "Immune Response to Cyclin B1 in Hepatocellular Carcinoma," *Hepatology*, (PubMed Abstract ID 8985268), 25(1): 75-80 (Jan. 1997).
Crystal et al., "Clinical Protocol, A Phase 1 Study, in Cystic Fibrosis Patients, of the Safety, Toxicity, and Biological Efficacy of a Single Administration of a Replication Deficient, Recombinant Adenovirus Carrying the cDNA of the Normal Cystic Fibrosis Transmembrane Conductance Regulator Gene in the Lung," *Human Gene Therapy*, 6(5): 643-666 (May 1995).
Crystal et al., "Clinical Protocol, Evaluation of Repeat Administration of a Replication Deficient, Recombinant Adenovirus Containing the Normal Cystic Fibrosis Transmembrane Conductance Regulator cDNA to the Airways of Individuals with Cystic Fibrosis," *Human Gene Therapy*, 6(5): 667-703 (May 1995).
Davis et al., "Anti-Idiotype Antibodies Can Induce Long-Term Complete Remissions in Non-Hodgkin's Lymphoma Without Eradicating the Malignant Clone," *Blood*, 92(4): 1184-1190 (Aug. 15, 1998).
De Boer et al., "Cyclin D1 Protein Analysis in the Diagnosis of Mantle Cell Lymphoma," *Blood*, 86(7): 2715-2723 (Oct. 1, 1995).
Derby et al., "Two intermediate-avidity cytotoxic T lymphocyte clones with a disparity between functional avidity and MHC tetramer staining," *International Immunology* 13(6): 817-824 (Jun. 2001).
Diefenbach et al., "Rae1 and H60 ligands of the NKG2D receptor stimulate tumour immunity," *Nature*, 413(6852): 165-171 (Sep. 13, 2001).
Disis et al., "HER-2/neu Oncogenic Protein: Issues in Vaccine Development," *Critical Reviews in Immunology*, 18(1&2): 37-45 (1998).
Dong et al., "Prognostic Significance of Cyclin E Overexpression in Laryngeal Squamous Cell Carcinomas," *Clinical Cancer Research*, 6(11): 4253-4258 (Nov. 2000).
Dudley et al., "A Phase I Study of Nonmyeloablative Chemotherapy and Adoptive Transfer of Autologous Tumor Antigen-Specific T Lymphocytes in Patients with Metastatic Melanoma," *Journal of Immunotherapy*, 25(3): 243-251 (May/Jun. 2002).
Dudley et al., "Cancer Regression and Autoimmunity in Patients After Clonal Repopulation with Antitumor Lymphocytes," *Science*, 298(5594): 850-854 (Oct. 25, 2002).
Dutta et al., "Cyclins as markers of tumor proliferation: Immunocytochemical studies in breast cancer," *Proc. Natl. Acad. Sci. USA*, 92(12): 5386-5390 (Jun. 6, 1995).
Eng et al., "An Approach to Correlate Tandem Mass Spectral Data of Peptides with Amino Acid Sequences in a Protein Database," *Journal of the American Society for Mass Spectrometry*, 5(11): 976-989 (Nov. 1994).
Engel et al., "High-Efficiency Expression and Solubilization of Functional T Cell Antigen Receptor Heterodimers," *Science*, 256(5061): 1318-1321 (May 29, 1992).
Eshhar et al., "The T-body approach: potential for cancer immunotherapy," *Springer Semin Immunopathol*, 18(2): 199-209 (1996).
European Patent Office, International Search Report dated Aug. 20, 2007, in PCT/US2005/044024.
European Patent Office, Supplementary Partial European Search Report dated Dec. 12, 2005, in 02797036.7.
Fay et al., "Long-term outcomes in patients with metastatic melanoma vaccinated with melanoma peptide-pulsed CD34[+] progenitor-derived dendritic cells," *Cancer Immunol. Immunother*, 55: 1209-1218 (2006).

(56) References Cited

OTHER PUBLICATIONS

Fernandez et al., "Dendritic cells directly trigger NK cell functions: Cross-talk relevant in innate anti-tumor immune responses in vivo," *Nat Med*, 5(4): 405-411 (Apr. 1999).

Finn et al., "MUC-1 Epithelial Tumor Mucin-Based Immunity and Cancer Vaccines," *Immunological Reviews*, 145: 61-89 (1995).

Fisk et al., "Identification of an Immunodominant Peptide of HER-2/neu Protooncogene Recognized by Ovarian Tumor-specific Cytotoxic T Lymphocyte Lines," *The Journal of Experimental Medicine*, 181(6): 2109-2117 (Jun. 1995).

Fontenot et al., "Biophysical Characterization of One-, Two-, and Three-Tandem Repeats of Human Mucin (muc-1) Protein Core," *Cancer Research*, 53(22): 5386-5394 (Nov. 15, 1993).

Fontenot et al., "Structure of a Tumor Associated Antigen Containing a Tandemly Repeated Immunodominant Epitope," *Journal of Biomolecular Structure & Dynamics*, 13(2): 245-260 (Oct. 1995).

Freshney, "Culture of Animal Cells," *Culture of Animal Cells, A Manual of Basic Technique*, (Freshney, ed.), 4 (Alan R. Liss, Inc., New York, N.Y., 1983).

Garcia et al., "An $\alpha\beta$ T Cell Receptor Structure at 2.5 Å and Its Orientation in the TCR-MHC Complex," *Science*, 274(5285): 209-219 (Oct. 11, 1996).

Gaugler et al., "Human Gene MAGE-3 Codes for an Antigen Recognized on a Melanoma by Autologous Cytolytic T Lymphocytes," *The Journal of Experimental Medicine*, 179: 921-930 (Mar. 1994).

Grégoire et al., "Covalent assembly of a soluble T cell receptor-peptide-major histocompatibility class I complex," *Proc. Natl Acad Sci U S A*, 93(14): 7184-7189 (Jul. 1996).

Groner et al., "Cytotoxic T-cells with grafted, tumor-specific recognition functions," *European Journal of Cancer*, 33: S20 (Jun. 1997).

Gura, "Systems for Identifying New Drugs Are Often Faulty," *Science*, 278: 1041-1042 (Nov. 7, 1997).

Hanenberg et al., "Colocalization of retrovirus and target cells on specific fibronectin fragments increases genetic transduction of mammalian cells," *Nature Medicine*, 2(8): 876-882 (Aug. 1996).

Hassan et al., "Clinical Significance of Cyclin B1 Protein Expression in Squamous Cell Carcinoma of the Tongue," *Clinical Cancer Research*, 7: 2458-2462 (Aug. 2001).

Henderson et al., "II Tumor Antigens Defined by Antibodies," *Advances in Immunology*, 62: 217-256 (1996).

Herman et al., "A peptide encoded by the human MAGE3 gene and presented by HLA-B44 induces cytolytic T lymphocytes that recognize tumor cells expressing MAGE3," *Immunogenetics*, 43(6): 377-383 (1996).

Herr et al., "Detection and quantification of blood-derived CD8+ T lymphocytes secreting tumor necrosis factor $\alpha$ in response to HLA-A2.1-binding melanoma and viral peptide antigens," *Journal of Immunological Methods*, 191(2): 131-142 (1996).

Hiltbold et al., "Presentation of MUC1 Tumor Antigen by Class I MHC and CTL Function Correlate with the Glycosylation State of the Protein Taken Up by Dendritic Cells," *Cellular Immunology*, 194(2): 143-149 (Jun. 15, 1999).

Holmberg et al., "High-dose busulfan, melphalan and thiotepa followed by autologous peripheral blood stem cell (PBSC) rescue in patients with advanced stage III/IV ovarian cancer," *Bone Marrow Transplant*, 22(7): 651-659 (Oct. 1, 1998).

Holmberg et al., "Clinical outcome of breast and ovarian cancer patients treated with high-dose chemotherapy, autologous stem cell rescue and THERATOPE® STn-KLH cancer vaccine," *Bone Marrow Transplant*, 25(12): 1233-1241 (Jun. 2, 2000).

Hunt et al., "Characterization of Peptides Bound to the Class I MHC Molecule HLA-A2.1 by Mass Spectrometry," *Science*, 255(5049): 1261-1263 (March 6, 1992).

Hunt et al., Peptides Presented to the Immune System by the Murine Class II Major Histocompatibility Complex Molecule I-A$^d$ *Science*, 256(5065): 1817-1820 (Jun. 26, 1992).

Ikeda et al., "Characterization of an Antigen that is Recognized on a Melanoma Showing Partial HLA Loss by CTL Expressing an NK Inhibitory Receptor," *Immunity*, 6: 199-208 (Feb. 1997).

International Search Report dated Aug. 20, 2007, in PCT/US2005/044024.

Jaffe et al., "Adenoviral Mediated Transfer and Expression of a Normal Human $\alpha$1-Antitrypsin cDNA in Primary Rate Hepatocytes," *Clinical Research*, 39(2): 302A (1991).

Jemal et al., "Cancer Statistics, 2003," *CA Cancer J Clin*, 53(1): 5-26 (Jan./Feb. 2003).

Jerome et al., "Cytotoxic T-Lymphocytes Derived from Patients with Breast Adenocarcinoma Recognize an Epitope Present on the Protein Core of a Mucin Molecule Preferentially Expressed by Malignant Cells," *Cancer Research*, 51(11): 2908-2916 (Jun. 1, 1991).

Jones et al., "Improved Methods for Building Protein Models in Electron Density Maps and the Location of Errors in these Models," *Acta Crystallographica*, A47, (Pt 2): 110-119 (Mar. 1, 1991).

Kao et al., "A New Strategy for Tumor Antigen Discovery Based on in Vitro Priming of Naïve T Cells with Dendritic Cells," *Clinical Cancer Research*, 7(3 Supplement): 773s-780s (Mar. 2001).

Kao et al., "Identification of Cyclin B1 as an Epitheliol Tumor Antigen," *FASEB Journal*, (Abstract 949.6) 15(5): A1206 (Mar. 8, 2001).

Kao et al., "Identification of Cyclin B1 as a Shared Human Epithelial Tumor-Associated Antigen Recognized by T Cells," *J. Exp. Med.* 194(9): 1313-1323 (Nov. 5, 2001).

Kawakami et al., "Identification of a human melanoma antigen recognized by tumor-infiltrating lymphocytes associated with in vivo tumor rejection," *Proc. Natl. Acad. Sci. USA*, 91(14): 6458-6462 (Jul. 5, 1994).

Kawakami et al., "Recognition of Multiple Epitopes in the Human Melanoma Antigen gp100 by Tumor-Infiltrating T Lymphocytes Associated with In Vivo Tumor Regression," *The Journal of Immunology*, 154(8): 3961-3968 (Apr. 15, 1995).

Kawamoto et al., "Expression of the G2-M Checkpoint Regulators Cyclin B1 and cdc2 in Nonmalignant and Malignant Human Breast Lesions," *The American Journal of Pathology*, 150(1): 15-23 (Jan. 1997).

Keyomarsi et al., "Redundant cyclin overexpression and gene amplification in breast cancer cells," *Proc. Natl. Acad. Sci. USA*, 90(3): 1112-1116 (Feb. 1, 1993).

Kiessling et al., "Immunosuppression in human tumor-host interaction: role of cytokines and alterations in signal-transducing molecules," *Springer Seminars in Immunopathology*, 18(2): 227-242 (1996).

Kim et al., "Cyclin E overexpression as an independent risk factor of visceral relapse in breast cancer," *European Journal of Surgical Oncology*, 27: 464-471 (2001).

King et al., "Mitosis in Transition," *Cell*, 79: 563-571 (Nov. 18, 1994).

Klug et al., "Inactivation of a GFP retrovirus occurs at multiple levels in long-term repopulating stem cells and their differentiated progeny," *Blood*, 96(3): 894-901 (Aug. 1, 2000).

Koehne et al., "Phenotype of lymphocyte subsets after autologous peripheral blood stem cell transplantation," *Bone Marrow Transplant*, 19(2): 149-156 (Jan. 2, 1997).

Kondo et al., "Biology of Hematopoietic Stem Cells and Progenitors: Implications for Clinical Application," *Annul Review of Immunology*, 21: 759-806 (2003).

Korean Intellectual Property Office, International Search Report dated Mar. 5, 2010, in PCT/US09/51853.

Kraulis et al., "MOLSCRIPT: a program to produce both detailed and schematic plots of protein structures," *Journal of Applied Crystallography*, 24(1): 946-950 (Feb. 1, 1991).

Kushner et al., "Aberrant expression of cyclin A and cyclin B1 proteins in oral carcinoma," *Journal of Oral Pathology & Medicine*, 28(2): 77-81 (Feb. 1999).

Lazar et al., "Transforming Growth Factor $\alpha$: Mutation of Aspartic Acid 47 and Leucine 48 Results in Different Biological Activities," *Molecular and Cellular Biology*, 8(3): 1247-1252 (Mar. 1988).

Lennette et al., "Antibodies to LMP2A/2B in EBV-carrying Malignancies," *European Journal of Cancer*, 31A(11): 1875-1878 (1995).

(56) References Cited

OTHER PUBLICATIONS

Lin et al., "Structure-Function Relationships in Glucagon: Properties of Highly Purified Des-His[1]-, Monoiodo- and [Des-Asn[28], Thr[29]](homoserine lactone[27])-glucagon," *Biochemistry*, 14(8): 1559-1563 (1975).

Luckow et al., "Trends in the Development of Baculovirus Expression Vectors," *Bio/Technology*, 6: 47-55 (Jan. 1988).

Lundstrom et al., "Latest development in viral vectors for gene therapy," *Trends in Biotechnology*, 21(3): 117-122 (Mar. 2003).

Maecker et al., "Use of overlapping peptide mixtures as antigens for cytokine flow cytometry," *Journal of Immunological Methods*, 255: 27-40 (2001).

Magarian-Blander et al., "Specific and Effective T-Cell Recognition of Cells Transfected with a Truncated Human Mucin cDNA," *Ann N Y Acad Sci*, 690: 231-243 (1993).

Magarian-Blander et al., "Differential expression of MUC1 on transfected cell lines influences its recognition by MUC1 specific T cells," *Glycoconjugate Journal*, 13: 749-756 (1996).

Magarian-Blander et al., "Intercellular and Intracellular Events Following the MHC-Unrestricted TCR Recognition of a Tumor-Specific Peptide Epitope on the Epithelial Antigen MUC1," *Journal of Immunology*, 160(7): 3111-3120 (Apr. 1, 1998).

Martin et al., "Subfemtomole MS and MS/MS Peptide Sequence Analysis Using Nano-HPLC Micro-ESI Fourier Transform Ion Cyclotron Resonance Mass Spectrometry," *Analytical Chemistry*, 72(18): 4266-4274 (Sep. 15, 2000).

Mashal et al., "Expression of Cell Cycle-regulated Proteins in Prostate Cancer," *Cancer Research*, 56: 4159-4163 (Sep. 15, 1996).

Medzhitov et al., "Innate Immunity: The Virtues of a Nonclonal System of Recognition," *Cell*, 91(3): 295-298 (Oct. 31, 1997).

Merrifield, "Solid Phase Peptide Synthesis. I. The Synthesis of a Tetrapeptide," *J. Am. Chem. Soc.*, 85: 2149-2154 (Jul. 20, 1963).

Merritt et al., "Raster3D: Photorealistic Molecular Graphics," *Methods in Enzymology*, 277: 505-524 (1997).

Mittelbrunn et al., "Cutting Edge: Dynamic Redistribution of Tetraspanin CD81 at the Central Zone of the Immune Synapse in Both T Lymphocytes and APC," *Journal of Immunology*, 169(12): 6691-6695 (Dec. 15, 2002).

Molloy et al., "Production of soluble single-chain T-cell receptor fragments in *Escherichia coli* trxB mutants," *Molecular Immunology*, 35(2): 73-81 (Feb. 1998).

Morgan et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens," *Journal of Immunology*, 171(6): 3287-3295.(Sep. 15, 2003).

Murakami et al., "Determination of the prognostic significance of cyclin B1 overexpression in patients with esophageal squamous cell carcinoma," *Virchows Arch*, 434: 153-158 (1999).

Murray, "Cyclin Ubiquitination: The Destructive End of Mitosis," *Cell*, 81: 149-152 (Apr. 21, 1995).

Musgrove et al., "Cyclins and Breast Cancer," *Journal of Mammary Gland Biology and Neoplasia*, 1(2): 153-162 (1996).

NCBI "Chain B, Crystal Structure of Phospho-Cdk2 In Complex with Cyclin B," Database Entrez-Nucleotide, Accession No. 2JGZ_B (Jun. 20, 2007). Retrieved on Feb. 27, 2010.

NCBI "Cyclin B1 [*Homo sapiens*]," Database Entrez-Nucleotide, Accession No. AAV38930.1 (Oct. 28, 2004). Retrieved on Feb. 27, 2010.

NCBI "*Homo sapiens* cyclin B1 (CCNB1), mRNA," Database Entrez-Nucleotide, Accession No. NM_031966.2 (Jul. 2, 2011). Retrieved on Jul. 7, 2011.

NCBI "Mus musculus cyclin B1 (Ccnb1), mRNA," Database Entrez-Nucleotide, Acciession No. NM_172301.3 (May 15, 2011). Retrieved on Jul. 7, 2011.

NCBI "Unnamed Protein Product [*Homo sapiens*]," Database Entrez-Nucleotide, Accession No. BAF82120.1 (Oct. 28, 2004). Retrieved on Feb. 27, 2010.

Novotny et al., "A soluble, single-chain T-cell receptor fragment endowed with antigen-combining properties," *Proc Natl Acad Sci U S A*, 88(19): 8646-8650 (Oct. 1991).

Ohashi et al., "Efficient transfer and sustained high expression of the human glucocerebrosidase gene in mice and their functional macrophages following transplantation of bone marrow transduced by a retroviral vector," *Proc Natl Acad Sci U S A*, 89: 11332-11336 (Dec. 1992).

Ostrand-Rosenberg, "Tumor immunotherapy: the tumor cell as an antigen-presenting cell," *Current Opinion of Immunology*, 6(5): 722-727 (1994).

Pavlinkova et al., "Pharmacokinetics and biodistribution of a light-chain-shuffled CC49 single-chain Fv antibody construct," *Cancer Immunology Immunotherapy*, 49(4-5): 267-275 (2000).

Pearlman et al., "AMBER, a package of computer programs for applying molecular mechanics, normal mode analysis, molecular dynamics and free energy calculations to simulate the structural and energetic properties of molecules," *Computer Physics Communications*, 91(1-3): 1-41 (Sep. 11, 1995).

Petit et al., "High level of single-nucleotide polymorphism in the rat cyclin B1 gene," *Mammalian Genome*, 10(6): 635-637 (1999).

Petri et al., "The Crystal Structure of Human Cyclin B," *Cell Cycle*, 6(11): 1342-1349 (Jun. 1, 2007).

Pinthus et al., "Immuno-Gene Therapy of Established Prostate Tumors Using Chimeric Receptor-redirected Human Lymphocytes," *Cancer Research*, 63(10): 2470-2476 (May 15, 2003).

Prosecution history of U.S. Appl. No. 10/253,867, filed Sep. 24, 2002, current as of present.

Prosecution history of U.S. Appl. No. 11/295,767, filed Dec. 7, 2005, current as of present.

Prosecution history of U.S. Appl. No. 11/366,196, filed Mar. 2, 2006, current as of present.

Prosecution history of U.S. Appl. No. 12/698,822, filed Feb. 2, 2010, current as of present.

Prosecution history of U.S. Appl. No. 13/055,907, filed Aug. 8, 2011, current as of present.

Ressing et al., "Human CTL Epitopes Encoded by Human Papillomavirus Type 16 E6 and E7 Identified Through In Vivo and In Vitro Immunogenicity Studies of HLA-A*0201-Binding Peptides," *The Journal of Immunology*, 154(11): 5934-5943 (Jun. 1, 1995).

Restifo et al., "Identification of Human Cancers Deficient in Antigen Processing," *Journal of Experimental Medicine*, 177(2): 265-272 (Feb. 1, 1993).

Robbins et al., "A Mutated β-Catenin Gene Encodes a Melanoma-specific Antigen Recognized by Tumor Infiltrating Lymphocytes," *The Journal of Experimental Medical*, 183(3): 1185-1192 (Mar. 1, 1996).

Röpke et al., "Spontaneous human squamous cell carcinomas are killed by a human cytotoxic T lymphocyte clone recognizing a wild-type p53-derived pepetide," *Proc. Natl. Acad. Sci. USA*, 93(25): 14704-14707 (Dec. 10,1996).

Rosenberg et al., "Treatment of Patients With Metastatic Melanoma With Autologous Tumor-Infiltrating Lymphocytes and Interleukin 2," *Journal of the National Cancer Institute*, 86(15): 1159-1166 (Aug. 3, 1994).

Rosenfeld et al., "In Vivo Transfer of the Human Cystic Fibrosis Gene to the Respiratory Epithelium," *Clinical Research*, 39(2): 311A (1991).

Rosenfeld et al., "Adenovirus-Mediated Transfer of a Recombinant α1-Antitrypsin Gene to the Lung Epithelium in Vivo," *Science*, 252(5004): 431-434 (Apr. 19, 1991).

Rubinstein et al., "Transfer of TCR Genes into Mature T Cells Is Accompanied by the Maintenance of Parental T Cell Avidity," *Journal of Immunology*, 170(3): 1209-1217 (Feb. 1, 2003).

Sadovnikova et al., "Generation of human tumor-reactive cytotoxic T cells against peptides presented by non-self HLA class I molecules," *Eur. J. Immunol.*, 28: 193-200 (1998).

Saio et al., "Tumor-Infiltrating Macrophages Induce Apoptosis in Activated CD8[+] T Cells by a Mechanism Requiring Cell Contact and Mediated by Both the Cell-Associated Form of TNF and Nitric Oxide," *Journal of Immunology*, 167(10): 5583-5593 (Nov. 15, 2001).

(56) References Cited

OTHER PUBLICATIONS

Sanderson et al., "LacZ inducible, antigen/MHC-specific T cell hybrids," *International Immunology*, 6(3): 369-376 (Mar. 1994).
Schafmeister et al., C.E.A.F., University of California, San Francisco, 1-191 (1995).
Schumacher, "T-Cell-Receptor Gene Therapy," *Nature*, 2: 512-519 (Jul. 2002).
Schwartz et al., "A superactive insulin: [B10-Aspartic acid]insulin(human)," *Proc. Natl. Acad. Sci. USA*, 84: 6408-6411 (Sep. 1987).
Shabanowitz et al., "Sequencing the Primordial Soup," *Mass Spectrometry in Biology and Medicine*, (Burlingame et al., eds.), 163-177 (Humana Press, Totowa, N.J., 2000).
Shively et al., "CEA-Related Antigens: Molecular Biology and Clinical Significance," *Critical Reviews in Oncology/Hematology*, 2(4): 355-399 (1985).
Shubert et al., "Rapid degradation of a large fraction of newly synthesized proteins by proteasomes," *Nature*, 404(6779): 770-774 (Apr. 13, 2000).
Skolnick et al., "From genes to protein structure and function: novel applications of computational approaches in the genomic era," *Trends in Biotech*, 18: 34-39 (Jan. 2000).
Slamon et al., "Use of Chemotherapy Plus a Monoclonal Antibody Against HER2 for Metastatic Breast Cancer That Overexpresses HER2," *New England Journal of Medicne*, 344(11): 783-792 (Mar. 15, 2001).
Snyder et al., "Molecular Mechanisms and Biological Significance of CTL Avidity," *Current HIV Research*, 1(3): 287-294 (2003).
Soria et al., "Overexpression of Cyclin B1 in Early-Stage Non-Small Cell Lung Cancer and Its Clinical Implication," *Cancer Research*, 60(15): 4000-4004 (Aug. 1, 2000).
Stanislawski et al., "Circumventing tolerance to a human MDM2-derived tumor antigen by TCR gene transfer," *Nature Immunology*, 2(10): 962-970 (Oct. 2001).
Steeg et al., "Cyclins and breast cancer," *Breast Cancer Research and Treatment*, 52: 17-28 (1998).
Supplementary Partial European Search Report dated Aug. 22, 2005, in 02797036.7.
Supplementary Partial European Search Report dated Dec. 12, 2005, in PCT/US02/30289.
Tran et al., "Mitotic Cyclins and Cyclin-Dependent Kinases in Melanocytic Lesions," *Human Pathology*, 29(10): 1085-1090 (Oct. 1998).
Traversari et al., A Nonapeptide Encoded by Human Gene MAGE-1 Is Recognized on HLA-A1 by Cytolytic T Lymphocytes Directed against Tumor Antigen MZ2-E, *The Journal of Experimental Medicine*, 176: 1453-1457 (Nov. 1992).
Türeci et al., "Serological analysis of human tumor antigens: molecular definition and implications," *Molecular Medicine Today*, 3(8): 342-349 (Aug. 1997).
U.S. Appl. No. 11/366,196, filed Mar. 2, 2006.
United States Patent and Trademark Office, International Search Report dated Oct. 8, 2003, in PCT/US02/30289.
Van Den Eynde et al., "A New Family of Genes Coding for an Antigen Recognized by Autologous Cytolytic T Lymphocytes on a Human Melanoma," *The Journal of Experimental Medicine*, 182: 689-698 (Sep. 1995).
Van Der Bruggen et al., "Autologous cytolytic T lymphocytes recognize a MAGE-1 nonapeptide on melanomas expressing HLA-Cw*1601*," *European Journal of Immunolgy*, 24(8): 2134-2140 (Sep. 1994).
Van Der Bruggen et al., "A peptide encoded by human gene MAGE-3 and presented by HLA-A2 induces cytolytic T lymphocytes that recognize tumor cells expressing MAGE-3," *European Journal of Immunology*, 24(10): 3038-3043 (Dec. 1994).
Vella, et al., "Healthy individuals have T-cell and antibody responses to the tumor antigen cyclin B1 that when elicited in mice protect from cancer," *PNAS*, 106(33): 14010-14015 (Aug. 18, 2009).
Vlad et al., "Complex Carbohydrates Are Not Removed During Processing of Glycoproteins by Dendritic Cells: Processing of Tumor Antigen MUC1 Glycopeptides for Presentation to Major Histocompatibility Complex Class-II restricted T Cells," *Journal of Experimental Medicine*, 196(11): 1435-1446 (Dec. 2, 2002).
Wang et al., "Human tumor antigens for cancer vaccine development," *Immunological Reviews*, 170: 85-100 (1999).
Wang et al., "Overexpression of cyclin B1 in human colorectal cancers," *Journal of Cancer Research and Clinical Oncology*, 123(2): 124-127 (1997).
Wang et al., "A T cell-independent antitumor response in mice with bone marrow cells retrovirally transduced with an antibody/Fc-γ chain chimeric receptor gene recognizing a human ovarian cancer antigen," *Nat Med*, 4(2): 168-172 (Feb. 1998).
Wang et al., "Cloning Genes Encoding MHC Class II-Restricted Antigens: Mutated CDC27 as a Tumor Antigen," *Science*, 284(5418): 1351-1354 (May 21, 1999).
Wang et al., "Prostate Antigen: A New Potential Marker for Prostatic Cancer," *The Prostate*, 2(1): 89-96 (1981).
Weijtens et al., "Functional balance between T cell chimeric receptor density and tumor associated antigen density: CTL mediated cytolysis and lymphokine production," *Gene Therapy*, 7(1): 35-42 (Jan. 2000).
Willemsen et al., "Grafting primary human T lymphocytes with cancer-specific chimeric single chain and two chain TCR," *Gene Therapy*, 7(16): 1369-1377 (Aug. 2000).
Willemsen et al., "Genetic Engineering of T Cell Specificity for Immunotherapy of Cancer," *Human Immunology*, 64(1): 56-68 (2003).
Wölfel et al., A $p16^{INK4a}$-Insensitive CDK4 Mutant Targeted by Cytolytic T Lymphocytes in a Human Melanoma, *Science*, 269(5228): 1281-1284 (Sep. 1, 1995).
Yang et al., "Antimelanoma Activity of CTL Generated from Peripheral Blood Mononuclear Cells After Stimulation with Autologous Dendritic Cells Pulsed with Melanoma gp100 Peptide G209-2M Is Correlated to TCR Avidity," *Journal of Immunology*, 169(1): 531-539 (Jul. 1, 2002).
Yasumura et al., "Human Cytotoxic T-Cell Lines with Restricted Specificity for Squamous Cell Carcinoma of the Head and Neck," *Cancer Research*, 53: 1461-1468 (Mar. 15, 1993).
Yee et al., "Adoptive T cell therapy using antigen-specific CD8+ T cell clones for the treatment of patients with metastatic melanoma: In vivo persistence, migration, and antitumor effect of transferred T cells," *Proc Natl Acad Sci U S A*, 99(25): 16168-16173 (Dec. 10, 2002).
Yu et al., "Aberrant cyclin B1 expression in human tumors and cell lines," *FASEB Journal*, (Abstract 949.5) 15(5): A1206 (Mar. 2001).
Yu et al., "Immune recognition of cyclin B1 as a tumor antigen is a result of its overexpression in human tumors that is caused by non-functional p53," *Molecular Immunology*, 38(12-13): 981-987 (May 2002).
Zeh III et al., "Flow-Cytometric Determination of Peptide-Class I Complex Formation Identification of p53 Peptides That Bind to HLA-A2," *Human Immunology*, 39(2): 79-86 (Feb. 1994).
U.S. Appl. No. 12/258,545, filed Oct. 27, 2008.
U.S. Appl. No. 11/295,767, filed Dec. 7, 2005.

* cited by examiner a

```
MA Vα23    QEVTQIPAALSVPEGENLVLNCSFTDSAIYN---LQWFRQDPGKGLTSLLLIQSSQREQTSGRLNASL
SM3L       DIVVTGESALTTSPGETVTLTCRSSTGAVTTSNYANWVQEKPDHLFTGLIGGTNNRAPGVPARFSGSL
                                                            CDR2

MA Vα23    DKSSGRTTLYIAASQPGDSATYLCAVTSSYGKLTFGQGTILTVHP
SM3L       --IGDKAALTITGAQTEDEAIYFCALWYS-NHWVFGGGTKLTVLG
                                    CDR3

MA Vβ8.3   DARVTGTPRHKVTEMGQEVTMRCQ--PILGHN-TVFWYRQTMMQGLELLQYFRNRAP---LDDSGMPK
SM3H       ------QESGGGLVQPGSMKLSCVASGFTFSNYWMNWVRQSPEKGLEWVAEIRLKSNNYATHYAESVK
                                                            CDR2

MA Vβ8.3   DRFSAEMPDATLAT-LKIQPSEPRDSAVYFCASGLGEASGYTFGSGTRLTV
SM3H       GRFTISRDDSKSSVYLQMNNLRAEDTGIYYCT-GVGQFA--YWGQGTTVTV
                                          CDR3
``` b

c
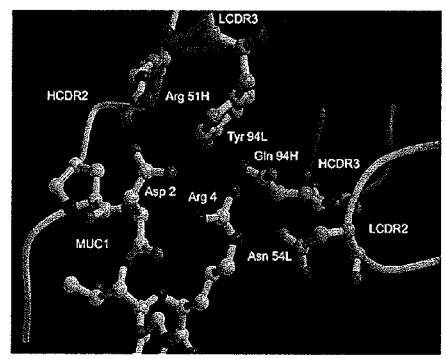

d

e
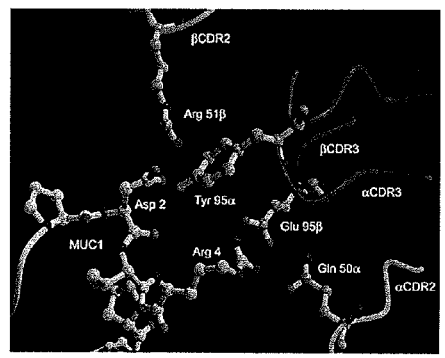

Fig. 1

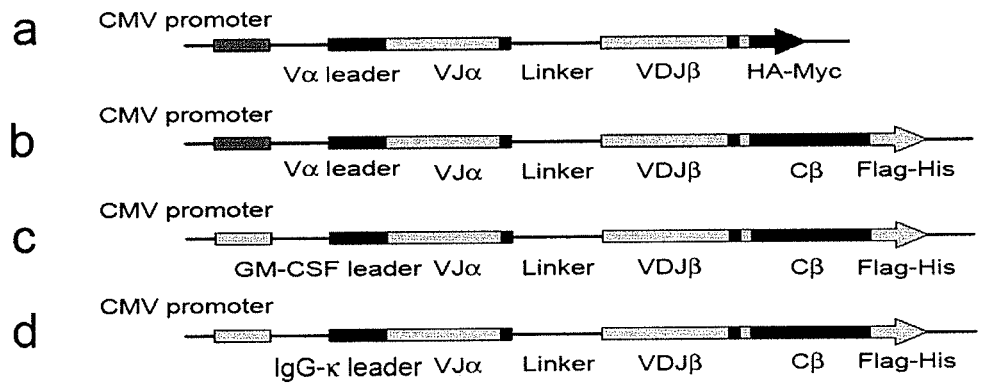
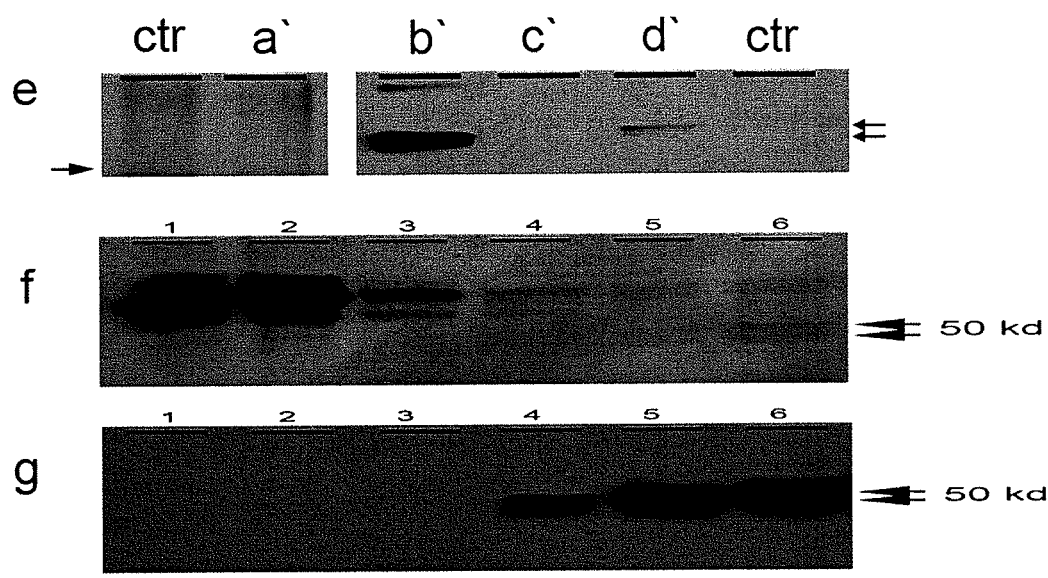
Fig. 15

THERAPEUTIC AND DIAGNOSTIC CLONED MHC-UNRESTRICTED RECEPTOR SPECIFIC FOR THE MUC1 TUMOR ASSOCIATED ANTIGEN

CROSS-REFERENCE TO RELATED APPLICATIONS

This application is a continuation of U.S. patent application Ser. No. 12/258,545, filed Oct. 27, 2008, which claims priority to U.S. patent application 11/295,767, filed Dec. 7, 2005 which claims priority to U.S. Provisional Patent Application 60/634,072, filed Dec. 7, 2004, the disclosure of each of which is incorporated herein in its entirety.

STATEMENT REGARDING FEDERALLY SPONSORED RESEARCH AND DEVELOPMENT

This invention was made with Government support under Grant Numbers CA56103 and predoctoral training grant DAMD17-99-1-9352 awarded by the U.S. National Institutes of Health and the U.S. Department of Defense, respectively. The United States Government has certain rights in the invention.

FIELD OF THE INVENTION

This invention pertains to the treatment or prevention of cancer in humans involving transfer of (a) an isolated population of cells, or (b) cells transduced with a nucleic acid encoding a receptor, into a human in need of treatment or prophylaxis for cancer. The present invention also pertains to a method of activating a signaling pathway.

BACKGROUND OF THE INVENTION

Immunotherapy of cancer involving adoptive transfer of T cells for various human tumor antigens has significantly improved in recent years. It has also recently become clear that immunotherapy is more potent if both the innate and the adaptive cellular immune responses are efficiently engaged. Timely recognition of the tumor by the cells of the innate immune system, such as NK cells, granulocytes, and macrophages, appears to be a prerequisite for an efficient stimulation of tumor-specific adaptive immunity.

Tumor-specific antibodies have been transduced into T cells (T-bodies) endowing the transduced T cells with MHC-unrestricted tumor antigen specificity. While antibodies can have exquisite specificity, one disadvantage is their high affinity of binding to antigen, which could impair infiltration of tumors, result in irreversible binding of an effector cell to a tumor cell, and possibly result in apoptosis of effector cells following their interaction with tumor cells. T cell receptors (TCRs), however, have a much lower binding affinity. Therefore, a cell bearing a tumor-specific TCR could engage and disengage from its target multiple times and effect its function against multiple tumor cells. Tumor specific T cells, however, are MHC-restricted. Accordingly, a tumor specific T cell is effective only for treatment of patients having a suitable human lymphocyte antigen (HLA). Additionally, tumor cells frequently down-regulate MHC or antigen processing molecules, thereby avoiding T cell recognition. Despite these limitations, adoptive immunotherapy therapies involving transfer of tumor-specific TCRs into T cells continue to be developed. Accordingly, the art is in need of an adoptive immunotherapy that can treat or prevent cancer in most or all patients. Desirably, such a therapy would not be dependent on the HLA or antigen processing components of target cancer cells. Moreover, it would be desirable if such a therapy caused little or no immune reaction with non-target cells.

BRIEF SUMMARY OF THE INVENTION

The invention provides a method of activating a signaling pathway in a cell. The method comprises transducing the cell with at least one nucleic acid that encodes a receptor so that the receptor is expressed and displayed on the surface of the cell. The encoded receptor is capable of binding to a MUC1 antigen without requiring the MUC1 antigen to be presented in the context of a major histocompatibility complex (MHC). The receptor either interacts with a signaling molecule, or comprises a signaling domain, such that when the receptor is contacted with a cell having the MUC1 tumor antigen on its surface, the signaling pathway is activated. In a preferred embodiment the receptor is a T cell receptor.

The encoded and expressed receptor can have any suitable sequence. For example, the receptor can have any sequence in which the affinity of the receptor for MUC1 is determined by a first amino acid sequence and a second amino acid sequence in which the first amino acid sequence consists essentially of the portion of MA Vα23 shown in FIG. 1 (SEQ ID NO:1) and the second amino acid sequence consists essentially of the portion of MA Vβ8.3 shown in FIG. 1 (SEQ ID NO:2).

The encoded receptor can also have a sequence that is at least 85% identical, at least 90% identical, at least 95% identical, or is essentially identical to the portions of MA Vα23 and MA Vβ8.3 shown in FIG. 1 (SEQ ID NOs:1 and 2, respectively).

The cell signaling can generate any useful response in the transduced cell, such as (without limitation) cytokine secretion and target cell killing (e.g., cancer cell killing).

The invention also provides a population of cells comprises a method of killing a cancer cell, the method comprising isolating a population of cells, such as T cells, that have a receptor that binds to a MUC1 tumor antigen independently of a major histocompatibility complex, and contacting the population of cells to a cancer cell expressing the MUC1 tumor antigen, thereby killing the cancer cell. The isolated population of cells preferably does not comprise a therapeutically-effective quantity of B cells, more preferably is substantially free of B cells, and even more preferably does not comprise B cells.

The invention also provides isolated nucleic acids encoding receptors that bind to the MUC1 tumor antigen even when the MUC1 tumor antigen is not presented in the context of an MHC. The encoded receptor preferably has at least one amino acid sequence that is homologous with, consists essentially of, or is identical with at least one of the amino acid sequences designated MA Vα23 or MA Vβ38.3 in FIG. 1 (SEQ ID NOs:1 and 2, respectively). The encoded receptor can be membrane bound when expressed in a cell or can be expressed in a water-soluble form.

The nucleic acid encoding the receptor can be transduced into a variety of cells. The transduced cells can be used for therapeutic purposes (such as the treatment or prevention of cancer), diagnostic purposes (such as the identification of the MUC1 tumor antigen), or as a tool in the study of T cell function and/or immunogene therapy.

The nucleic acids (e.g., alone or in the context of a gene delivery vector), isolated populations of cells, and transduced cells of the invention can be combined with sterile carriers, pharmaceutically acceptable excipients, or adjuvants, each of which is preferably suitable for administration to a human.

The receptor can also be isolated or substantially purified, and combined with a labeling agent to provide a reagent useful in the detection of the MUC1 tumor antigen in a suitable sample.

These and other advantages of the invention, as well as additional inventive features, will be apparent from the description of the invention provided herein.

BRIEF DESCRIPTION OF THE DRAWINGS

FIG. 1 depicts a comparison of the CDR2 and CDR3 regions of the MUC1-specific antibody SM3 and the MA TCR and modeling their interactions with MUC1. FIG. 1a Amino acid sequence alignment of MA Vα23 (SEQ ID NO:1) and MA Vβ8.3 (SEQ ID NO:2) with SM3L and SM3H (SEQ ID NOs:23 and 24, respectively). Numbering corresponds to MA TCR sequence. Residues in bold are hypothesized to be involved in the binding (FIG. 1b, and FIG. 1c) SM3 and (FIG. 1d, and FIG. 1e). MA TCR computer based models of the interactions with the MUC1 epitope. Contact residues are shown as stick diagrams.

FIG. 2a shows mammalian expression vector encoding MA scTCR gene. The scTCR was cloned into the pEF6 vector. FIG. 2b shows cell surface expression of the scTCR in RBL cells and FIG. 2c shows BWZ cells stably transfected with the scTCR-pEF6 vector. Cells were stained with anti-TCR βF1 (open histogram) or with isotype control (filled histogram) antibody. FIG. 2d shows degranulation of RBL cells (open bar) or RBL-scTCR cells (striped bar) following stimulation with plate-bound βF1 antibody or MUC1 140mer peptide. Specific-degranulation is presented as percent of maximum degranulation induced by TCR cross-linking with βF1 antibody. FIG. 2e shows IL-2 ELISA for BWZ (open bars) or BWZscTCR (striped bar) following stimulation with plate-bound anti-TCR βF1 antibody, ionomycin+PMA (I/P), DM6 (MUC1$^-$ tumor), HPAF or T3M4 (MUC$^+$ tumors). IL-2 in culture supernatant was measured by ELISA and values were plotted on the y-axis as pg/ml. Cells were stimulated as indicated.

FIG. 3a shows a schematic diagram of the scTCR-EGFP MFG retroviral vector. FIG. 3b shows Bone Marrow (BM) cells transduced with the scTCR-EGFP MFG retroviral vector were stained on day 7 in culture for hematopoietic stem cells surface markers (c-Kit and Sca-1), and for lineage markers (Lin). Cells that expressed high levels of Sca-1 and c-Kit (c) and that lacked expression of Lin (d), R2 & R3 were gated on and were plotted against EGFP (FIG. 3e). FIG. 3f shows mock transduced BM cells. All cells in culture were Thy1.1$^-$ (not shown).

(FIG. 4a) GR-1 for granulocytes, (FIG. 4b) mac-3 or F4/80 for monocyte/macrophages, (FIG. 4c) DX5 for NK cells, (FIG. 4d) CD3 for T cells, and (FIG. 4e) B220 for B cells. EGFP expression is plotted on the x-axis. Percentages of EGFP positive cells in each lineage are indicated.

FIG. 5a shows control (filled triangles) or scTCR-reconstituted (open circles) mice were injected subcutaneously with 2×10$^6$ HPAF (MUC1$^+$) tumor cells. Tumor size is shown on the y-axis while days post-tumor challenge is plotted on the x-axis. P-Values were calculated by running t-test using Microsoft Excel software. Data are presented as mean±S.E. FIG. 5b shows H & E staining of HPAF tumor sections from control mice (left panel) or from scTCR-reconstituted mice (right panel). FIG. 5c shows staining of tumor sections from scTCR-reconstituted mice for myeloperoxidase (neutrophils marker), F4/80 (monocytes/macrophage marker), or Granzyme B (NK cells marker). Images were taken under 20× magnification. Images in the lower right squares were taken under 100× magnification.

FIG. 6A shows C57BL/6 (wild type) and MUC1 Tg. mice were reconstituted with BM cells transduced with the scTCR-EGFP MFG retroviral vector. Untreated mice served as controls. Spleen, lung, and pancreas were harvested 6 weeks postreconstitution and microscopically examined for infiltration with EGFP$^+$ cells (FIG. 6a) or stained with H&E (FIG. 6b) and examined for tissue destruction.

FIG. 8a shows expression of scTCR mRNA in transduced BM cells 72 hours post-transduction. FIG. 8b shows expression of scTCR mRNA was in splenocytes 60 days post-reconstitution. M is 1 Kb DNA molecular weight marker. β-actin is the RT-PCR control.

FIG. 12E shows quantitative comparison of TCR expression on 293H cells transfected with different scTCR constructs. p<0.05.

(FIG. 13A) Rat Basophilic Leukemia (RBL) or mouse T cell tumor BWZ cells were transfected with the scTCR-pEF6 and stained for surface expression with anti-TCR βF1 antibody (filled) or with isotype control (open) histogram. FIG. 13B shows IL-2 secretion from BWZ cells (open bars) or BWZ-scTCR (filled bars) following stimulation with SEE superantigen or with anti-TCR βF1 antibody.

FIG. 14A shows scTCR expression vector encoding a thrombin cleavage site, T. FIG. 14B shows RBL cells transfected with the scTCR were stained with anti-TCR βF1 antibody (open histograms) before (right) or after (left) treatment with thrombin. The filled histogram shows staining with isotype control antibody. FIG. 14C shows immunoprecipitation of the scTCR from RBL (lanes 1 and 2) or RBL cells transfected with the scTCR (Lanes 2 and 4) before (lanes 1 and 2) or after (lanes 3 and 4) treatment with thrombin. Lane 6-8 are SA-HRP blotting of fraction eluted with 150 mM Glycine, PH 2.2, 100 mM Glycine pH 2.2, or diethyl amine (DEA) pH 11.2, respectively. Lane 5 is IP from control lysate.

FIG. 15 shows expression and purification of soluble scTCR using a mammalian expression system. FIG. 15a shows the single chain fraction variable (scFV) domain was cloned and fused to a C-terminus HA and c-myc epitope tags. FIG. 15b shows secreted scTCR (sscTCR) that was cloned and fused to a C-terminus Flag and 6-His epitope tags. FIGS. 15c and 15d show the sscTCR as described in FIG. 15b, except fused to the leader sequence from GM-CSF (FIG. 15c) or from Ig-κ light chain (FIG. 15d). FIG. 15e shows a western blot of the culture supernatants from 293H cells transiently transfected with constructs a-d (a'-d'), immunoprecipitated with appropriate anti-tag antibody and blotted with anti-c-myc antibody (a') or with anti FLAG-M2 antibody (b'-d'). "Ctr." is supernatant from untransfected cells. (f) Comassiee blue staining of fractions from culture supernatant b' purified using nickel column. Lane 1 is culture supernatant before purification, 2 is flow through, 3 is wash, and 4-6 are different eluted fractions. FIG. 15g shows a western blot of panel f using anti-Flag M2 antibody.

DETAILED DESCRIPTION OF THE INVENTION

Figure 2:
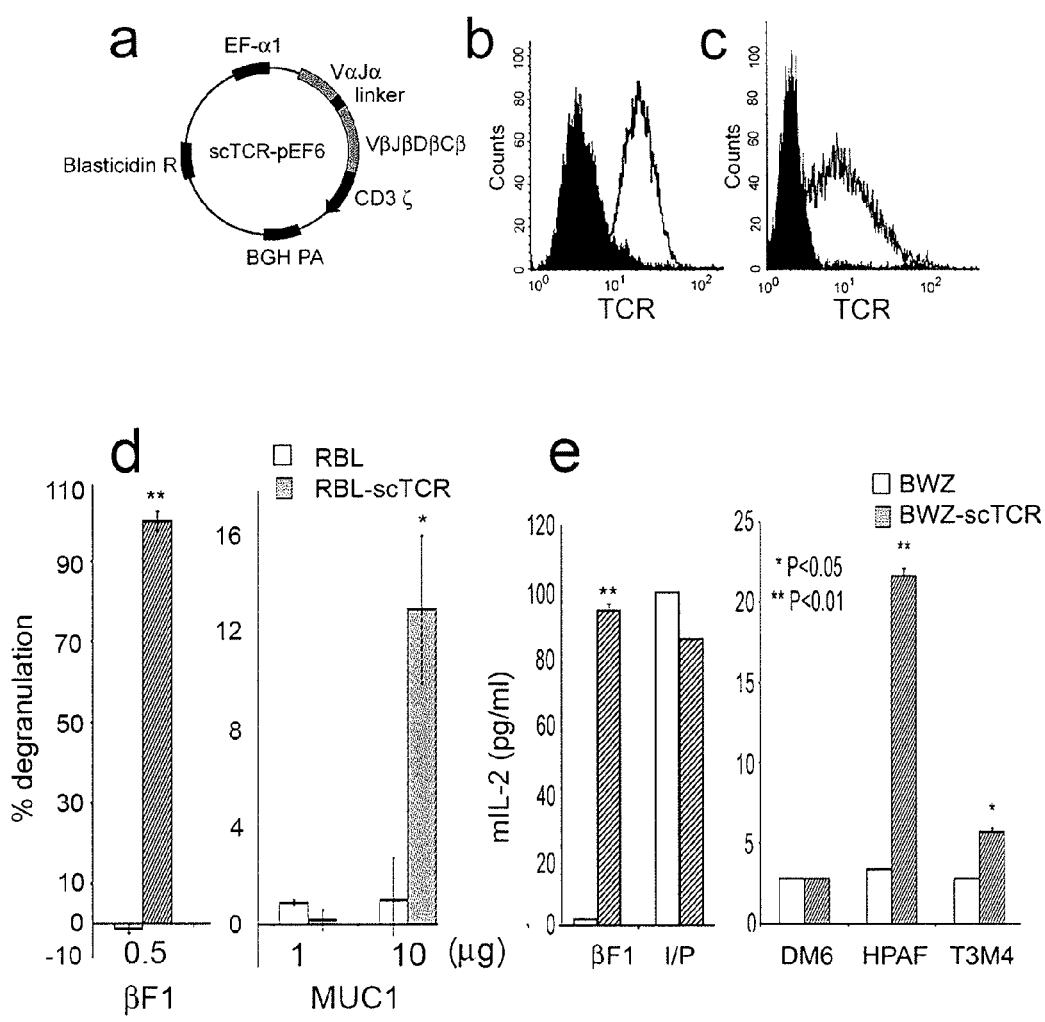
FIG. 2 depicts cells transfected with scTCR recognize MUC1$^+$ tumors and synthetic MUC1 antigen.

The MA TCR referenced in FIG. 1 is a T cell receptor (TCR) that binds to the MUC1 tumor antigen. The MA TCR recognizes an epitope located in each of the 20 amino acid long tandem repeats in the extracellular domain of MUC1. Each molecule of MUC1 can have more than 100 repeats. The amino acid sequence critical for recognition by the TCR is believed to be a five amino acid residue sequence (PDTRP SEQ ID NO: 3) which has been called the immmunodominant knob of the MUC1 protein. A large number of these tandemly repeated and structurally stable PDTRP (SEQ ID NO: 3) bearing knobs on a single MUC1 molecule, as well as on neighboring MUC1 molecules on the surface of a tumor cell, can engage multiple TCRs, and signal a T cell to effect its function. While not desiring to be bound by any particular theory, it is believed that the MA TCR can effectively bind with the MUC1 tumor antigen without requiring antigen processing and presentation in an MHC, which is required by most T cell receptors. While the MA TCR referenced in FIG. 1 is a preferred TCR that is capable of recognizing the MUC1 tumor antigen independently of presentation by an MHC, functionally similar TCRs can be raised against the MUC1 tumor antigen or any other disease associated antigen with structurally stable, repeated amino acid epitope similar to MUC1. The antigen binding domains of these TCRs readily can be incorporated into a variety of receptor constructs such that a cell expressing the receptor will have at least one signaling pathway activated when contacted to a cell having the MUC1 or other structurally stable, repeated amino acid epitope on its surface.

Accordingly, the invention provides a method of activating a signaling pathway in a cell. The method comprises transducing the cell with at least one nucleic acid encoding a receptor that binds to the MUC1 tumor antigen independently of presentation of the MUC1 tumor antigen in the context of an MHC. The signaling pathway is activated when the receptor is expressed and displayed on the surface of the transduced cell, and the transduced cell is contacted to a cell having the MUC1 tumor antigen on its surface. Of course, the transduced cell can be a T cell, but as is further described below, any suitable cell or collection of cells can be transduced.

The invention also provides an isolated nucleic acid encoding the receptor. Nucleic acids suitable in the context of the invention include natural and synthetic nucleic acids. Natural nucleic acids can be DNA or RNA irrespective of whether they are isolated directly from a cell, e.g., an MA T cell clone, synthesized by chemical or other means, or carried in a vector. Artificial nucleic acids can include regions of natural polynucleotides and can further comprise 2' methyl nucleic acids, 2' methoxy nucleic acids, phosphorothiorated nucleic acids, nucleotides comprising synthetic or modified bases (e.g., inosine), peptidyl nucleic acids (PNAs) and other synthetic nucleic acids known in the art, so long as the nucleic acid can be transcribed, if necessary, and translated into a receptor. The receptor encoded by the isolated nucleic acid is preferably not an antibody or immunoglobulin. Similarly, the receptor preferably does not have a constant region of any antibody.

The sequence of the receptor does not need to be identical to that of the MA TCR. In fact, amino acid substitutions can be made or allowed in both the affinity determining regions of the MA TCR and in the framework regions of the TCR. Additionally, domains of other proteins can be incorporated into the receptor. Accordingly, the invention also provides a method of activating a signaling pathway comprising transducing a cell with a nucleic acid encoding a receptor having affinity for the MUC1 tumor antigen, wherein the affinity of the receptor for the MUC1 tumor antigen is determined by a first amino acid sequence consisting essentially of the portions of MA Vα23 and MA Vβ8.3 shown in FIG. 1 (SEQ ID NOs:1 and 2, respectively).

Additionally, the invention provides a method of activating a signaling pathway or of killing a cancer cell wherein the transduced cell, or population of cells, comprises a receptor having at least one amino acid sequence that has at least 85%, optionally at least 90%, or optionally at least 95% identity with the portion of MA Vα23 shown in FIG. 1 (SEQ ID NO:1). The receptor can also have a sequence that is identical with the portion of MA Vα23 shown in FIG. 1 (SEQ ID NO:1). The receptor preferably also has at least one amino acid sequence that has at least 85%, optionally at least 90%, or optionally at least 95% identity with the portion of MA Vβ8.3 shown in FIG. 1 (SEQ ID NO:2), or which is identical with the portion of MA Vβ8.3 shown in FIG. 1 (SEQ ID NO:2). More preferably, the receptor comprises both amino acid sequences.

As used herein, a sequence is 85% identical to another sequence if, in a window comprising the number of amino acids present in the named sequence, at least 85% of the amino acids, allowing gaps or insertions within the window (but not allowing the number of amino acids in the window to exceed the number of amino acid residues in the test sequence) are the same as those in the other sequence. For example, the portion of MA Vα23 shown in FIG. 1 has 110 amino acid residues. Accordingly, a sequence is 85% identical with the portion of MA Vα23 if at least 94 residues in any 110 consecutive residues of one sequence can be exactly aligned with 110 consecutive residues of the other sequence.

The receptor can also be any receptor having an amino acid sequence comprising the complementarity determining regions (CDRs) of MA Vα23 or MA Vβ8.3 or both.

The invention also provides a method of killing a cancer cell. The cancer cell can be present in a culture of cells in vitro or found in an animal's (e.g., a human's) body. The method of killing the cancer cell involves isolating a population of cells comprising a receptor that binds to a MUC1 tumor antigen independently of an MHC and contacting a portion of the cells from the isolated population of cells to a cancer cell. The population of cells can be created by transduction of one or more cells of an animal with a nucleic acid of the invention. In another alternative, an animal can be immunized with the MUC1 tumor antigen to raise lymphocytes comprising a receptor that mediates the death of cells expressing the MUC1 tumor antigen. While not desiring to be bound by any particular theory, it is believed that the highly repetitive nature of the MUC1 epitope enables the routine generation of T cells expressing receptors for the MUC1 antigen that are MHC unrestricted. Of course, the population of cells can comprise T cells or consist essentially of T cells. The population of cells also can be isolated or manipulated in such a way that the population does not comprise any cells other than T cells that comprise a receptor that binds to a MUC1 tumor antigen independently of an MHC. In one embodiment, for example, the population of cells does not comprise B cells having a B cell receptor (BCR) that is specific for the MUC1 tumor antigen.

The receptor can have any suitable affinity for the MUC1 tumor antigen. For example, the affinity of the receptor can be higher than the affinity of the MA TCR for the MUC1 tumor antigen. Receptors having lower affinity for the MUC1 tumor antigen than the MA TCR are also useful in the context of the present invention. However, the receptor preferably has about the same affinity of the MUC1 tumor antigen as the MA TCR because this level of affinity is high enough to efficiently invoke effector functions of T cells, while simultaneously allowing efficient tumor infiltration and avoiding apoptosis of the cell on which it is displayed. While receptors having other affinities for the MUC1 tumor antigen are useful, receptors having a $K_d$ of between 0.2 µM and 200 µM, are among the preferred embodiments. The affinity can be measured with a variety of conventional techniques. Preferably, however, the receptor is converted into a soluble form (if necessary) to measure its affinity. The skilled artisan will appreciate that conventional techniques employing a Biacore® device are particularly well suited to the measurement of receptor affinities for the MUC1 tumor antigen (Molloy et al., *Molecular Immunology*, 35: 73-81 (1998)).

The transduced cell, or a cell of the isolated population of cells, desirably has a suitable avidity for a cancer cell expressing the MUC1 tumor antigen. For example, the avidity between the transduced cell, or cell of the isolated population, can be between $1\times10^{-5}$ M and $1\times10^{-12}$ M.

The receptor can be encoded by 1, 2, or more nucleic acids. Any receptor (or nucleic acid encoding a receptor) having the antigen determining regions of the MA TCR is suitable in the context of the invention, including (but not limited to) a receptor encoded by a single nucleic acid, such as, but not limited to, a single-chain receptor in which the regions of the receptor having homology to the α-chain and the β-chain of the MA TCR are encoded as a single polypeptide. The receptor can also be an scFv. In other embodiments, the receptor can be encoded as at least two subunits. The receptor desirably has amino acid sequences derived from the Vα, Jα, Vβ, Dβ, and Jβ mature gene segments of the MA receptor. Additionally, the receptor preferably does not have light and heavy chains of an antibody, nor truncated polypeptides derived from light and heavy chains or the nucleic acids encoding the same.

In a preferred embodiment the receptor comprises at least one polypeptide that is fused to, or connected with, a portion of the zeta-chain of CD3. Many suitable configurations exist. In a preferred embodiment, the transmembrane and cytoplasmic domains of the zeta-chain of a CD3 molecule are fused to the α-constant domain of a TCR or, more preferably, a β-constant domain of a TCR. While not desiring to be bound by any particular theory, it is believed that the fusion of a portion of the CD3 zeta-chain to the remainder of the receptor facilitates surface expression of the receptor on a transduced cell. In a more preferred embodiment, the constant domain of the TCR and the portion of the CD3 zeta-chain are separated by an amino acid linker (also known as an amino acid spacer) encoded by a nucleic acid encoding the entire receptor or a portion of the receptor. The linker can be any suitable sequence, but is preferably selected to have a flexible structure. Any number of amino acid residues can be included in the linker but typically the linker will comprise at least one, more typically at least three, yet more typically at least about eight, and commonly at least about 12 amino acid residues. Additionally, the linker will typically not comprise more than about 30 amino acid residues, more commonly not more than about 22 amino acid residues, and commonly not more than about 18 amino acid residues. A linker having about 15 amino acid residues is among the more preferred embodiments. Additionally, the linkers primary function is to provide a flexible linkage between two portions of the receptor. Accordingly, the linker can optionally not have one or more functions selected from the group consisting of an immunological function, a membrane anchoring function, a membrane spanning function, a dimerization function, a signaling function, and an intracellular trafficking function. In contrast, however, the receptor can have amino acid sequences in additional to the linker which provide at least one of these functions. The linker preferably allows a high level of receptor expression when the receptor is expressed in a T cell or other suitable cell in comparison to an otherwise identical receptor that lacks the linker.

In another embodiment, the receptor comprises the transmembrane region from a CD4 molecule.

In embodiments comprising portions of a CD3 or a CD4 molecule the portions of these molecules can contain substantial variations from their natural sequences. For example, the portions of the CD3 or CD4 molecules can have at least about 65% identity, at least about 80% identity, or be essentially identical to a consensus sequence (also known as "wild type") human CD3 or CD4 molecule.

The nucleic acid encoding the receptor can be carried by any suitable vector. The vector is preferably a gene transfer vector (also known as a gene delivery vector). Suitable gene transfer vectors include both viral and non-viral vectors. Suitable viral vectors include, but are not limited to, retroviral vectors. Suitable viral vectors include, but are not limited to adenoviral vectors, adeno-associated viral vectors, and herpes viral vectors. Lentiviral vectors, particularly those having the ability to efficiently transduce quiescent cells are among the more preferred viral vectors. Other preferred vectors in the context of the present invention include liposomal vectors and MFG vectors.

The nucleic acids encoding a receptor having affinity for the MUC1 tumor antigen of the invention can be transduced into a stem cell, preferably a bone marrow stem cell. Advantageously, this enables the generation of a wide variety of cell types expressing the receptor, each of which has a high potential for propagation. Similarly, the cells can be removed from an animal and transduced in vitro. When the cells are transduced in vitro they need not be, but optionally can be, expanded (i.e., propagated) in vitro prior to their transfer into a host animal such as a human. Any suitable technique can be used to propagate the cells in vitro. Suitable methods include, but are not limited to culturing the cells with cytokines, stimulatory molecules (e.g., stimulatory antibodies), live, attenuated, or killed cells having the MUC1 tumor antigen on their surface. Preferably, the cells are autologous, which means that they are transferred into the host from which they were obtained. Transduced autologous cells are believed to be less likely to be rejected by the host animal into which they are transduced.

Conveniently, the nucleic acid(s) encoding the receptor can be transduced into the cells in vivo. While not desiring to be bound by any particular theory, it is believed that the transduced cells will find cells expressing the MUC1 tumor antigen on their surface, if present, and be stimulated to expand to reach therapeutic levels when a therapeutic quantity of cells is not transduced directly.

The cell can be transduced in a mixed population of cells, or can be partially or substantially purified prior to transduction with the nucleic acid encoding the receptor. A preferred cell type for transduction is the fibroblast. Fibroblasts are capable of rapid expansion and transduced fibroblasts treat and prevent cancer in patients having cancer cells that expresses the MUC1 tumor antigen.

The transduced cells can also be of the hematopoietic lineage. Hematopoietic cells that can be usefully transduced in the context of the present invention include T cells, B cells, NK cells, macrophages, granulocytes, and dendritic cells.

In a preferred embodiment, the cell to be transduced is removed from an animal (e.g., a human or other animal), the animal is treated for cancer, e.g., with chemotherapy or radiation or both. The chemotherapy and/or radiation optionally can be potent enough to decimate or destroy the patient's lymphocyte population. Then, the transduced cells are returned to the patient. Before, during, or after the transduced cells are transferred to the patient or other animal, the patient or other animal can be treated with cytokines that expand the population of lymphocytes (e.g., IL-2). Additionally, other therapeutic agents such as antiemetics, erythropoietin or other red blood cell boosters, hormones, and antibodies can also be administered to the patient or animal before, during, or after the transfer of the transduced cells to the patient or animal. Similarly, the animal can be treated with a vaccine, which vaccine is preferably a vaccine promoting a reaction against a tumor or cancer cell, and more preferably is a MUC1 vaccine. The MUC1 vaccine stimulates cells reactive with MUC1 to persist, or preferably, to propagate. Suitable MUC1 vaccines can comprise at least one PDTRP (SEQ ID NO: 3) sequence, which pentapeptide optionally can be found in the context of from about 5 to about 20 amino acids having identity with a naturally-occurring MUC-1 polypeptide known in the art. Such a vaccine preferably would comprise a multiplicity of PDTRP (SEQ ID NO: 3) amino acid sequences so that a MUC1 reactive cell would be presented with an array of reactive epitopes. For example, the vaccine can be configured to present reactive cells with 2, 3, 4, 5, 6-10, 11-20, or more PDTRP (SEQ ID NO: 3) epitopes in an array or complex, preferably on the surface of a cell. The vaccine can further comprise an excipient, sterile carrier or adjuvant.

In embodiments in which contact of the receptor with the cell having a MUC1 tumor antigen on its surface activates a signaling pathway, the signaling pathway can be of any suitable type. For example, the signaling pathway can cause the secretion of a cytokine or induce a cytotoxic response leading to the death of the cell displaying the MUC1 tumor antigen. Similarly, activation of the signaling pathway can lead to the secretion of a biomolecule, such as a endocrine, paracrine, autocrine, whether steroidal, peptidyl, or other, an enzyme, a carbohydrate, a proinflammatory or anti-inflammatory molecule, or a drug agent. In a preferred embodiment, the biomolecule causes the death of a cancer cell or attenuates the symptoms of cancer.

The receptor encoded by any nucleic acid of the invention can also be substantially purified or isolated from the cell expressing it, irrespective of whether the receptor is water-soluble or has a high affinity for cellular membranes (or artificial membranes such as micelles).

The inventive receptor can also be complexed with a labeling agent. Such receptor-labeling agents complexes are useful for the visualization or detection of cells expressing a MUC1 tumor antigen. A labeling agent can be directly detectable or indirectly detectable. For example, directly detectable labeling agents include (without limitation) a protein such as green fluorescent protein (i.e., GFP), a radioactive atom, or a gold microparticle can be attached to the receptor. Each of these moieties can be directly detected with suitable, conventional methods. Alternatively, the label can be an indirect label such as (without limitation) an enzyme (e.g., horse radish peroxidase), an antibody hapten (e.g., the well-known FLAG epitope, biotin, avidin, or streptavidin, or the like. The complex can be covalently or non-covalently bound as long as the complex remains associated during any detection steps. Additionally, the complex can be, but need not be, purified or substantially isolated from a cell expressing the receptor.

In view of the foregoing, the invention also provides an isolated cell that is optionally transduced with a nucleic acid of the invention, and encodes a receptor of the invention.

Any of the nucleic acids, cells, or population of cells of the invention can be combined with a sterile carrier, pharmaceutically acceptable excipient, or adjuvant, each of which is preferably suitable for administration to a mammal, and in particular a human. The composition can comprise a buffer, and the buffer or composition is preferably substantially isotonic with human blood (e.g., is isotonic with 0.7 M to 1.1 M $NaCl_2$).

Suitable methods of administering the nucleic acids of the invention to a mammal for purposes of gene therapy are known (see, e.g., Rosenfeld et al., *Science,* 252, 431-434 (1991); Jaffe et al., *Clin. Res.,* 39, 302A (1991); Rosenfeld et al., *Clin. Res.,* 39, 311A (1991); Berkner, *BioTechniques,* 6, 616-629 (1988); Crystal et al., *Human Gene Ther.,* 6, 643-666 (1995); Crystal et al., *Human Gene Ther.,* 6, 667-703 (1995)). Innate and adaptive cells can be found in most locations in the mammalian body. Accordingly, any suitable route of administration can be used. Intravenous administration of cells is preferred when the mammal is human. A particular route can provide a more immediate and more effective reaction than another route. Pharmaceutically acceptable excipients also are well-known to those who are skilled in the art, and are readily available. The choice of excipient will be determined in part by the particular method used to administer the recombinant vector. Accordingly, there is a wide variety of suitable formulations for use in the context of the invention.

Moreover, to optimize the ability of vectors, and particularly viral vectors, to enter a cell by the method of the invention, preferably the method is carried out in the absence of neutralizing antibodies directed against the particular vector being introduced intracellularly, which could impede transduction of target cells. The ordinarily skilled artisan can routinely test for the presence of such neutralizing antibodies. Techniques are also known in the art to prevent the presence of neutralizing antibodies from impeding effective protein production (see, e.g., International Patent Application WO 96/12406).

The following methods, formulations, and excipients for administering the inventive nucleic acids, vectors, and cells are merely exemplary and are in no way limiting.

Formulations suitable for oral administration of the nucleic acids and vectors can consist of (a) liquid solutions, such as an effective amount of the compound dissolved in diluents, such as water, saline, or orange juice; (b) suspensions in an appropriate liquid; and (c) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients.

Preferred formulations include aqueous and non-aqueous, isotonic sterile injection solutions, which can contain anti-oxidants, buffers, bacteriostats, and solutes that render the formulation isotonic with blood, and aqueous and non-aqueous sterile suspensions that can include suspending agents, solubilizers, thickening agents, stabilizers, and preservatives. The inventive nucleic acids and vectors can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The nucleic acids, vectors and cells of the invention can be formulated in unit-dose or multi-dose sealed containers, such as ampules and vials, and can be stored frozen. These nucleic acids, vectors and cells of the invention can be stored in light-resistant packaging, employing for example, colored glass vials or cardboard boxes. Similarly, instructions for use of the compositions, which preferably comply with the regulations of the U.S. Food and Drug Administration, and more preferably also with its European and Japanese equivalent agencies, can be included with these compositions. These nucleic acids, vectors and cells of the invention are preferably also free from non-recombinant microbes (including without limitation fungi and mycobacteria) and non-recombinant viruses. Preferably, the instructions suggest the use a certain quantity of one of these compositions (or range of quantities), or suggest administration of the composition to a mammal for research or therapy via a particular route of administration.

Additionally, a cell, and more preferably, a nucleic acid or vector of the invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the invention will vary with the inventive embodiment, the composition employed, the method of administration, and the particular site and organism being treated. However, the dose should be sufficient to provide a therapeutic response.

Any suitable number of transduced cells, or isolated cells, can be administered to a mammal. While a single cell of the innate or adaptive immune system is capable of expanding and providing a benefit, when the transduced or isolated cell is not a stem cell, it is preferable to administer at least $10^3$, more preferably at least $10^5$, even more preferably at least $10^8$ and optionally $10^{12}$ or more transduced T cells. One preferred embodiment of the invention comprises administration of from about $10^8$ to about $10^{12}$ transduced cells to a human. There is no theoretical upper limit on the number of transduced T cells that can be administered to a mammal or the number of times that T cells can be administered to a mammal. The ordinarily skilled artisan will appreciate, however, that the excessive quantities of administered transduced or isolated cells (e.g., in some embodiments more than $10^{18}$ transduced cells) can exceed the mammal's ability to support them, lead to undesirable clinical sequelae, and unnecessarily increase costs. Similarly, excessive administrations of therapeutic compositions to mammals can lead to undesirable effects such as allergic responses and infection, and so are preferably avoided.

A composition comprising transduced cells can be prepared so that it does not contain living cells other than blood cells and lymphocytes. That is, the composition can be sterile except for the transduced or isolated cells. Such compositions can be readily prepared by positive and negative selection of the desired cells from a population of cells transduced with the inventive nucleic acids or vectors. Suitable positive selection techniques include bioaffinity separations, which are well known in the art. For example, an antibody specific for a cell surface antigen of a desired cell can be linked to a magnetic bead, incubated with the transduced population, separated therefrom and optionally washed. Similarly, undesired cells can be eliminated from the composition by any suitable technique. Suitable negative selection techniques include immunomagnetic removal of undesired cells, and the use of antibiotics to destroy microbes. Moreover, leukophoresis, other filtration techniques, sterile technique, differential centrifugation, and other conventional methods can be used to produce a composition suitable for administration to a human.

In embodiments in which the mammal is subjected to lymphodepletion and cytokine or growth factor stimulation, any suitable regimen can be used. Dudley et al., *Science,*

298: 850-854 (2002), Rosenberg et al., *J. Natl. Cancer Inst.*, 86: 1159-1166 (1994) and Dudley et al., *J. Immunother.*, 25: 243-251 (2002), as well as other references described in these references, discuss one suitable lymphodepletion and IL-2 stimulation regimen. These references suggest, for example, treatment of a human with cyclophosphamide (about 60 mg/kg) and fludarabine (about 25 mg/m$^2$) and high-doses of IL-2 (i.e., about 720,000 IU/kg). Administration of IL-2 is preferably repeated multiple times and more preferably repeated 3 to 15 times, and is preferably administered 1-5 times daily, which numbers can be selected and adjusted within the discretion of the skilled medical artisan.

EXAMPLE 1

This example shows that a TCR with unique MHC-unrestricted antigen binding properties for the tumor antigen MUC1 binds its epitope on the MUC1 protein without the requirement of processing and presentation. This example also shows that a single chain Vα/Vβ/Cβ (scTCR) fused to a CD3 zeta-chain (ζ-chain) facilitates expression on the surface of cells of the innate immune system (e.g., granulocytes, macrophages, natural killer cells (NK cells)) as well as the adaptive immune system (e.g., T cells and B cells). This example additionally shows that cells of the innate immune system reject a tumor when provided with a tumor-antigen specific TCR. Also, this example shows that bone marrow cells transduced with a gene transfer vector encoding a T cell-related receptor specific for the MUC1 tumor antigen can improve the health of a mammal having cancer in which the cancer expresses a MUC1 tumor antigen. This example also shows that expression of the MUC1 tumor antigen specific receptor of the invention on large percentages of cells does not result in infiltration or destruction of tissues expressing normal MUC1. Additionally, this example shows that long-term expression of the inventive receptor can be achieved, particularly by transducing a suitable stem cell.

The following sections describe the Materials and Methods used in this example.

Computer Modeling. The amino acid sequence of the SM3 antibody shown in FIG. 1 was provided by Dr. J. Taylor-Papadimitriou, of the Imperial Cancer Research Fund. The Protein Data Bank at the Research Collaboratory for Structural Bioinformatics (www.rcsb.org/pdb) was searched for best-fit sequence alignments with the binding domain of the SM3 antibody using BLAST. Coordinates of a crystallized human α/β TCR heterodimer were provided by Dr. Ian Wilson, of the Scripps Clinic. Modeling studies were conducted on a Silicon Graphics Indigo workstation. Homolog templates were mutated and initial models were constructed using the program O (Jones, et al., *Acta Crystallogr A* 47 (Pt 2):110-119 (1991)). The programs LEaP (Schafmeister, et al. "LeAP", *University of California, San Francisco* (1995)) and AMBER/Interface were used to import protein database (PDB) files created by O into AMBER, which was used for global energy minimizations and molecular dynamics of selected loops and modeling of ligand binding (Pearlman, et al. *Computer Physics Communications* 91: 1-41 (1995)). The previously solved structure of the MUC1 epitope, PDTRP (SEQ ID NO: 3), and its 4 flanking amino acids (Fontenot et al. *J Biomol Struct Dyn* 13: 245-260 (1995)) was initially positioned in the antigen-binding region by rigid body docking using O. This positioning was followed by energy minimization and molecular dynamics in AMBER to allow the MUC1 epitope to position itself within the antigen-binding cleft. Figures were constructed using Molscript and Raster3D (Kraulis, et al., *Journal of Applied Crystallography* 24: 946-950 (1991), Merritt, et al. *Methods in Enzymology* 277: 505-524 (1997)).

Construction of scTCR and Expression in RBL and BWZ Cells. The RNA encoding the Vα23.1Jα14.3 of the MA TCR was cloned from the MA CTL clone by RT-PCR and ligated in frame to the TCR Vβ8.3DβJβ1.2 region using a 15 amino acid (aa) flexible linker encoding sequence GGG GSG GGG SGG GGS (SEQ ID NO: 4). The cloned sequence encoding the Vα23.1Jα14.3-linker-Vβ8.3DβJβ1.2 polypeptide was then cloned into a vector encoding the human TCR fragment Cβ2, followed by a polypeptide linker, GDLVPRGSSRLD (SEQ ID NO: 5) and the murine CD3 ζ-chain (obtained from Dr. A. J. McMichael, Weatherall Institute of Molecular Medicine, John Radcliffe Hospital, Oxford, UK) (Callan, et al., *Eur Immunol* 25: 1529-1534 (1995)). The last cysteine in the Cβ2 region was mutated to alanine using site directed mutagenesis to prevent dimerization of the scTCR. The construct was then cloned into the pEF6 mammalian expression vector (Invitrogen, Carlsbad, Calif.). RBL cells were obtained from Dr. Richard Klausner (while at NCI), and BWZ murine T cells were obtained from Dr. Nilabh Shastri (University of California, Berkeley). RBL cells were grown in cDMEM-10 medium (Mediatech Inc., Herndon, Va.; DMEM+10% FBS, 2 mM L-glutamine, 100 U/ml Penicillin, 100 U/ml streptomycin, 10 μM 2-ME, 1× non-essential amino acids, and 1× sodium pyruvate), while BWZ cells were grown in cRPMI-10. RBL and BWZ cells were transfected by electroporation using Bio-Rad Gene Pulser II (Bio-Rad Laboratories, Hercules, California) at 960 μF and 200 V settings.

Basophil Degranulation Assay. RBL cells or RBL-scTCR were incubated with $^3$H-serotonin (New England Nuclear Corp., Boston, Mass.) for 24 hours. After washing, cells were transferred to plates coated with βF1 antibody or with MUC1 140mer synthetic peptide (seven repeats of the sequence PDTRPAPGSTAPPAHGVTSA (SEQ ID NO: 6)). Plates were centrifuged briefly and incubated for 30 minutes at 37° C. Ice-cold PBS (Sigma) was added and the supernatant was harvested after additional centrifugation. Radioactivity was measured using a Wallac 1205 betaplate liquid scintillation counter (Gaithersburg, Md.).

IL-2 ELISA. BWZ or BWZ-scTCR cells were plated in U-bottom 96 well plates at $1\times10^5/200$ μl of cRPMI-10 medium, and $2\times10^4$ tumor cells (irradiated 6000 rad) were added as stimulators. Thirty six hours later, the amount of mIL-2 released in the medium was measured using a mouse IL-2 OptEIA kit (BD Pharmingen), according to the manufacturer's recommendations.

Construction of scTCR-EGFP MFG Retroviral Vector and Production of Viral Supernatant. The MFG retroviral vector was obtained from Dr. Paul Robbins (University of Pittsburgh, Pittsburgh, Pa.). The IRES-EGFP cassette was cloned by PCR from the pIRES2-EGFP vector (Clontech Laboratories, Palo Alto, Calif.) into the MFG retroviral vector downstream of the scTCR gene. The GP+E-86 ecotropic retroviral packaging cells (American Type Culture Collection, Manassas, Va.) were transfected with the scTCR-EGFP MFG vector and cultured for 5 days, followed by sorting the EGFP$^{high}$ population. Sorted cells were then cultured in DMEM-15 (DMEM+15% FBS, 2 mM L-glutamine, 100 U/ml Penicillin, 100 U/ml streptomycin) and thirty six hours later, retroviral supernatant was harvested and frozen at −80° C. until use.

Retroviral Transduction of BM Cells. All experiments in animals were performed under an approved protocol No. 0304530A-1 of the University of Pittsburgh IACUC. Six to eight week old SCID or Balb/c mice (Jackson Laboratory, Bar Harbor, Me.) were injected intraperitoneally with 150 mg/kg 5-FU (Invivogen, San Diego, Calif.). Five days later, mice were sacrificed and BM cells were isolated and pre-stimulated for 72 hours in the presence of 50 ng/ml rSCF, 10 ng/ml rmIL-3 and 10 ng/ml rmIL-6 (PeproTech Inc., Rocky Hill, N.J.) in DMEM-15. BM cells were resuspended in retroviral supernatant supplemented with 50 ng/ml rSCF, 10 ng/ml rmIL-3, 10 ng/ml rmIL-6 and polybrene at 8 µg/ml. In all BM transduction experiments, cells were plated in 24-well plates pre-coated with recombinant fibronectin CH-296 fragment (Takara Bio Inc, Madison, Wis.). Cells were then centrifuged for 30 minutes at RT at 800×g in a Sorvall T6000B centrifuge and put back in culture at 37° C. Transduction was repeated every 12 hours for a total of 4 cycles.

Reconstitution of Irradiated Mice with Transduced BM Cells and Flow Cytometric Analyses. Transduced BM cells were resuspended in PBS at $1 \times 10^7$/ml, and 200 µl of cell suspension was injected via the tail vein into irradiated recipient mice. SCID mice received a single dose of 350 rad while Balb/c mice were given a split dose of 900 rad total (50/50) 3 hours apart. Reconstituted mice were maintained in a germ-free environment and were put on acidified water (pH 2.5) for 3 weeks post-reconstitution. At 3, 6, and 11 weeks post-reconstitution, 200 µl of blood was collected via tail artery and cells were stained with the appropriate anti-surface marker antibody, PE-conjugated anti-CD3, -B220, -GR-1, -Mac-3 and -DX5 and APC-conjugated anti-F4/80 (eBiosciences, San Diego, Calif.), and analyzed on the Becton-Dickinson FACSCalibur (BD Biosciences, San Jose, Calif.).

Tumor Challenge and Immunohistochemistry. Mice reconstituted with BM cells transduced with scTCR-MFG or with a control supernatant were challenged subcutaneously with various numbers of HPAF tumor cells 5 weeks post-reconstitution. Tumor size was measured every 2-3 days using calipers. Tumors harvested from control or treated mice were fixed in 10% formalin, paraffin embedded, and sections were stained with H&E, anti-Myeloperoxidase (Labvision, Fremont, Calif.), anti-Granzyme B (Labvision), or anti-F4/80 (ebiosciences) in the Department of Pathology core facility, University of Pittsburgh.

Fluorescent Microscopic Analyses of Tissue Sections from Reconstituted Mice. Six weeks post-reconstitution, C57BL/6 mice or MUC1 Tg. mice reconstituted with scT-CREGFP transduced BM cells were sacrificed and spleen, lung, and pancreas were harvested and fixed in 2% PFA in PBS. Tissues were then frozen, sectioned and visualized for infiltration with EGFP+ immune cells at the Center for Biologic Imaging, University of Pittsburgh.

Statistics. Statistical analysis was done using Microsoft Excel and Graphpad Prism (GraphPad Software, San Diego, Calif.) software.

Figure 8:
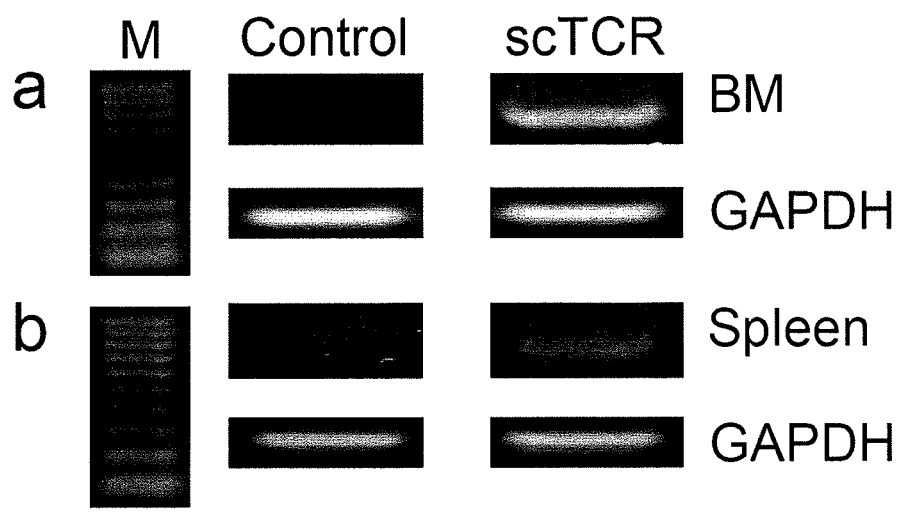
FIG. 8 shows RT-PCR analyses of scTCR expression in transduced BM cells and in splenocytes from reconstituted SCID mice.
Figure 9:
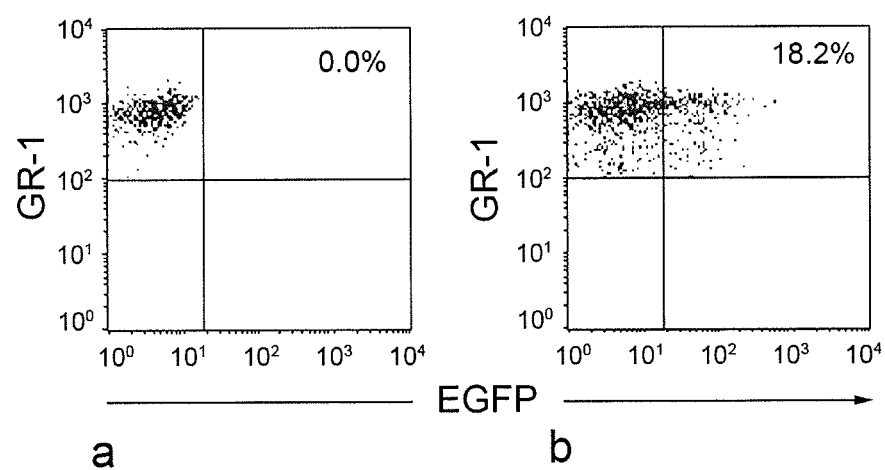
FIG. 9 shows long-term expression of scTCR in mice reconstituted with scTCR-transduced BM cells. Control (FIG. 9a) or scTCR-reconstituted mice (FIG. 9b) were bled 7 months post-reconstitution and were stained for GR-1. Cells were gated on GR-1+ and were plotted against EGFP.

In other experiments, we used live imaging microscopy to show the specificity of the MA TCR for MUC1 by the ability of transfected cells to flux calcium following stimulation with MUC1+ tumor. One data set shows that control-transfected JRT3-T3.5 didn't flux calcium in response to stimulation with MUC1+ tumor line (HPAF). A second data set shows that JRT3-T3.5 cells transfected with the TCR α and β chain from the MUC1-specific CTL clone (MA) fluxed calcium in response to stimulation with HPAF tumor line. FIG. 8 shows the detection of the scTCR mRNA in transduced BM cells as well as in splenocytes from SCID mice reconstituted with BM cells transduced with scTCR-MFG retroviral vector weeks post-reconstitution. FIG. 9 shows long-term expression of the scTCR on granulocytes in reconstituted C57BL/6 mice 7 months post-reconstitution.

The following section describes the RESULTS obtained in this example.

Computational Modeling of MA TCR Binding to the MUC1 "Immunodominant Knob" Shows Similarity to the Binding of SM3 Antibody Specific for the Same Epitope.

MUC1 specific MHC unrestricted CTL clone MA established from a tumor-draining lymph node of a breast cancer patient was previously described (Magarian-Blander et al., *J. Immunol.* 160: 3111-3120 (1998)). This clone mediated TCR-dependent killing of MUC1+ tumor cells that was not restricted by their HLA type. It was also capable of binding synthetic, tandemly repeated MUC1 epitopes immobilized on the surface of Polylactide-L-Glycolide (PLGA) beads, resulting in the influx of $Ca^{2+}$. Semi-quantitative RT-PCR analysis and DNA sequencing revealed that the TCR responsible for this binding was composed of Vα23.1Jα14.3 and Vβ8.3DβJβ1.2. We cloned this TCR and transduced the TCR-deficient Jurkat cell line (J.RT3-T3.5) (Ohashi et al., *Proc Natl Acad Sci. (USA)* 89: 11332-11336 (1992)) with a plasmid vector encoding the full length TCR α and β chains. Its functionality and specificity were confirmed by live imaging microscopy, where TCR-transfected cells, but not control cells, fluxed $Ca^{2+}$ upon binding to MUC1+ human tumor cells.

The antibody SM3 recognizes the same epitope, and blocks tumor cell recognition and killing by MHC-unrestricted MUC1-specific CTL. Considering the common epitope recognized by both SM3 and MA TCR, their common Ig-like fold, and similarities in the CDR3 sequences (FIG. 1a), we used the available sequence and structural information to model antigen binding by these two functionally related receptors. Both SM3 and the MA TCR were modeled by homology using appropriate antibody templates. Simulated docking of the MUC1 epitope produced minimized structures of both SM3 and MA TCR with bound ligand and predicted similar molecular determinants in the CDR2 and CDR3 regions important for binding. Our models predict that similarly positioned arginines in the corresponding Vβ and $V_H$ CDR2s interact favorably with the aspartic acid in the MUC1 epitope PDTRP (FIGS. 1b-1e). Equivalently positioned tyrosines in the corresponding Vα and $V_L$ CDR3s stabilize the interaction with the aspartic acid of MUC1. A glutamine in the αCDR2 and a glutamic acid in the βCDR3 interact with the arginine in the epitope, as do an asparagine in the VL CDR2 and a glutamine in the VH CDR3.

MA TCR as a Single-Chain (scTCR) Construct Fused with Zeta (ζ) Chain is Functionally Expressed on the Surface of T and Non-T Cells. To create a more practical reagent for future gene therapy/immunotherapy applications, we converted the full length two-chain TCR, which is dependent on CD3 molecules unique to T cells for cell surface expression, into a CD3 independent single-chain TCR (scTCR). The VαJα segment was fused to the VβDβJβ segment using a 15 amino acid flexible linker. This chimeric structure was then cloned into a vector containing the human TCR Cβ2 and the CD3 ζ transmembrane and cytoplasmic domains separated by a short linker, and further subcloned into the pEF6 plasmid to create scTCR-PEF6 mammalian expression vector (FIG. 2a). Transfection of the scTCR-PEF6 into a CD3− rat basophil cell line RBL (FIG. 2b) or a CD3+ mouse T cell lymphoma line BWZ (FIG. 2c) resulted in high surface expression of the scTCR, in both cell types.

These same two cell lines were used to test the function and antigen specificity of the scTCR. Transfected RBL degranulated upon cross-linking of their scTCR with the anti-TCR antibody βF1 or upon specific recognition of the MUC1 antigen (FIG. 2d). No degranulation was seen when cells were stimulated with control antigen ovalbumin. There was no degranulation in control untransfected RBL upon encounter with either MUC1 or βF 1 antibody. Similarly, transfected BWZ cells produced a substantial amount of IL-2 when their scTCR was cross-linked with plate-bound βF1 antibody (FIG. 2e). No significant IL-2 production was detected when BWZ-scTCR cells were incubated with the DM6 tumor cell line that did not express MUC1; however, substantial level of IL-2 was produced upon encounter with MUC1$^+$ tumor cell lines HPAF and T3M4. These two cell lines do not share HLA alleles confirming that cells expressing the cloned scTCR exhibit the same MHC-unrestricted recognition of MUC1 as the original T cell clone from which the TCR was derived. The difference in IL-2 secretion in response to these two tumors can be attributed to frequently observed differences in the level of expression and the extent of glycosylation of MUC1 on different tumor cell lines.

Figure 3:
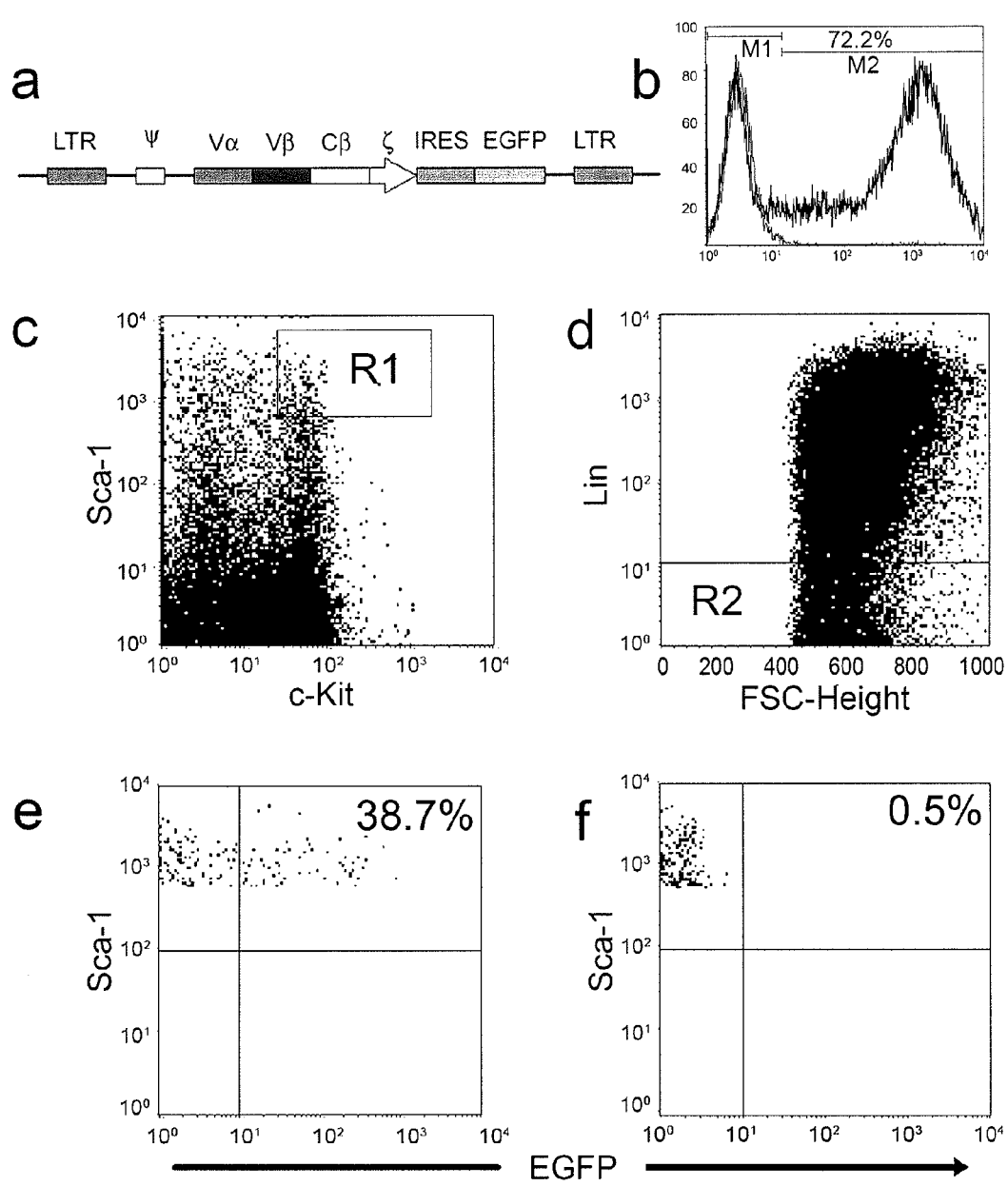
FIG. 3 shows transduction of the long-term reconstituting hematopoietic stem cell population (c-Kit$^+$ Sca-1$^+$Lin$^-$ Thy1.1$^-$) with scTCR-EGFP MFG retroviral vector.

Transduction of Bone Marrow (BM) cells that Differentiate In Vivo into scTCR$^+$ Cells of Multiple Hematopoietic Lineages. In order to test the anti-tumor activity of this MUC1-specific TCR in vivo, we cloned the scTCR into the MFG retroviral vector with an EGFP gene downstream of an IRES sequence (FIG. 3a). We used the green fluorescence of EGFP to track scTCR transduced cells. BM cells were isolated from 5-FU treated Balb/c mice and transduced with the scTCR-EGFP MFG retroviral vector using fibronectin-assisted transduction protocol. Seventy-two percent of BM cells were successfully transduced (FIG. 3b). We were especially interested in our ability to transduce hematopoietic stem cells contained within the population of cells that are Thy1.1$^-$Lin$^-$c-Kit$^+$ Sca-1$^+$. Thirty-eight percent (38%) of cells of that phenotype were successfully transduced (FIG. 3e).

Figure 4:
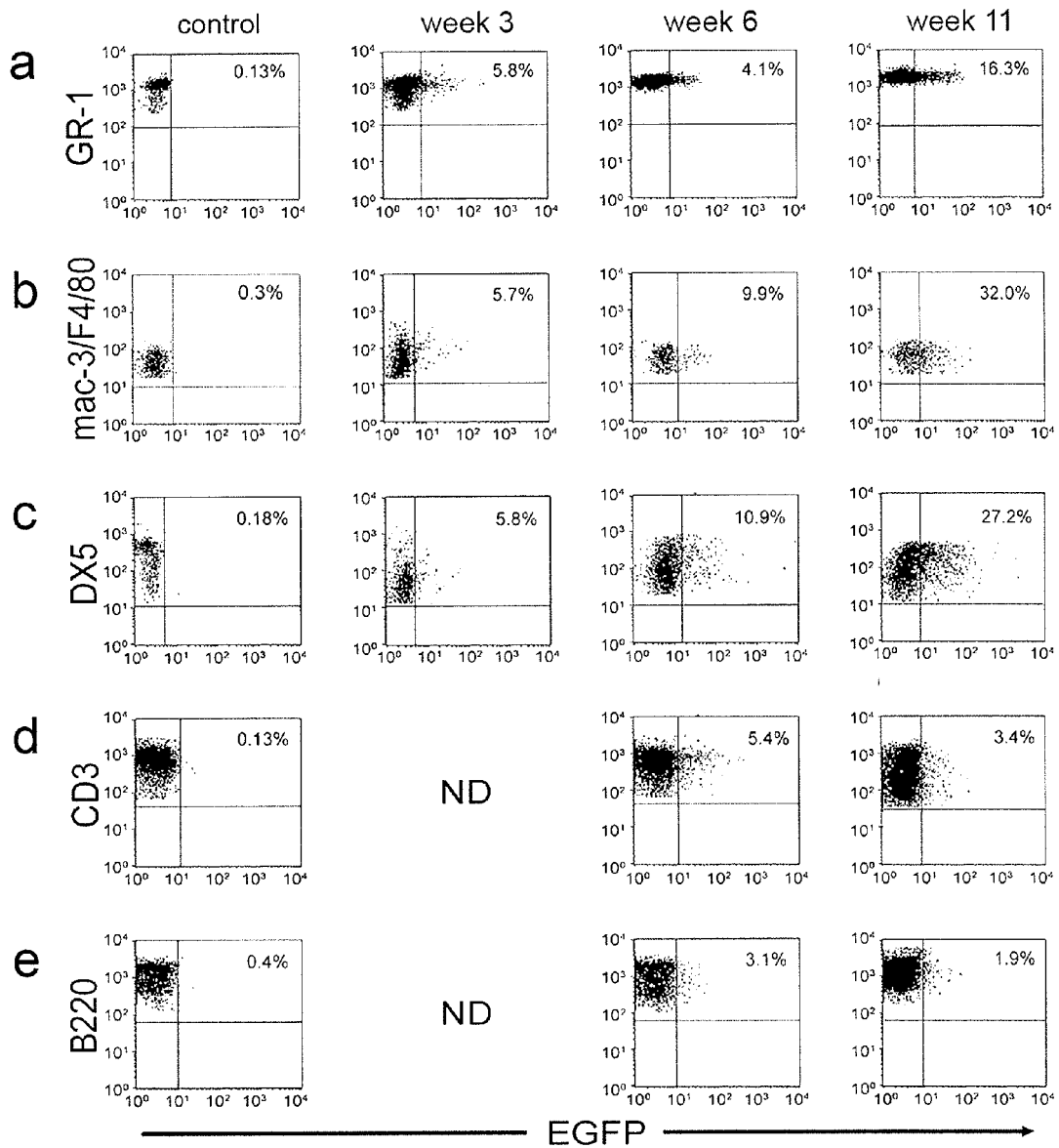
FIG. 4 shows detection of scTCR-expressing cells at various times post reconstitution with transduced BM cells. Mice were bled at indicated time points and leukocytes were stained for the appropriate cell surface markers plotted on the Y-axis.

Sub-lethally irradiated mice received 2×10$^6$ BM cells via tail vein injection. At 3, 6, and 11 weeks post-injection, mice were bled and the percentages of EGFP$^+$ cells in different cell lineages were evaluated. At week 3 post-reconstitution, 5.8% of granulocytes (GR-1$^+$) were positive for EGFP (FIG. 4a). This number increased to 16.3% at week 11. Reconstitution of the monocyte/macrophage (FIG. 4b) and NK cell (FIG. 4c) lineage followed similar kinetics. Transduced T cells (CD3$^+$) were seen in the periphery at week 6 post-reconstitution and accounted for 5.4% (FIG. 4d) of all T cells. This number dropped to 3.4% at week 11. Similarly, at 6 weeks, 3.4% of B cells (B220$^+$) expressed EGFP (FIG. 4e) and this number dropped to 1.9% at 11 weeks. This is consistent with published reports that lymphoid cells transduced with retroviral vectors have the tendency to silence expression of genes driven by the LTR promoter.

Figure 5:
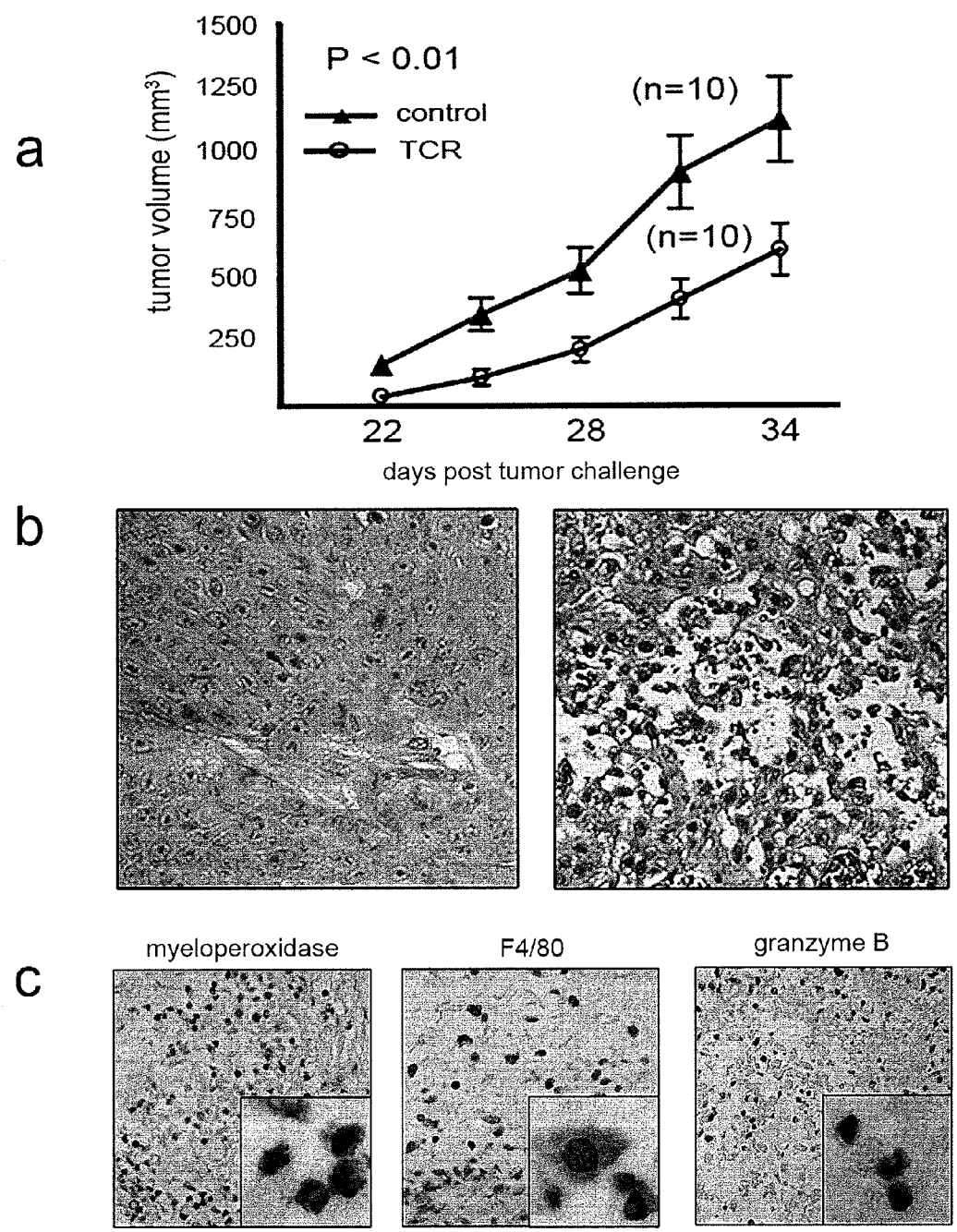
FIG. 5 shows SCID mice reconstituted with transduced BM cells can control the growth of the MUC1$^+$ tumor xenograft.

SCID Mice Reconstituted with the scTCR Transduced BM Controlled Outgrowth of a MUC1$^+$ Human Tumor. Based on our findings that the highest percent of cells expressing the scTCR were those of the innate immune system, and that this expression was most stable, we tested the potential of these cells alone to exert an anti-tumor effect. We reconstituted lethally irradiated SCID mice with 2×10$^6$ BM cells transduced with the scTCR-MFG retroviral vector or mock-transduced. Expression of the scTCR was detected by RT-PCR in transduced BM cells prior to injection and in splenocytes from reconstituted mice 60 days later (Figure). Mice reconstituted with BM cells transduced with the scTCR retroviral vector or with control supernatant were challenged one month later with subcutaneous injection of MUC1$^+$ human tumor cell line HPAF. Mice that received scTCR-MFG transduced BM cells were able to inhibit growth of HPAF tumor cells compared to control mice (FIG. 5a). The difference in tumor size between the two groups was statistically significant at each time point (p<0.01).

Tumor sections from control mice were intact and homogeneous in appearance, without any infiltration by immune cells (FIG. 5b, left panel). In contrast, tumor sections from scTCR BM reconstituted mice were almost completely destroyed and infiltrated with various immune cells (FIG. 5b, right panel). The predominant cells in the infiltrate were neutrophils (FIG. 5c, left) followed by macrophages (FIG. 5c, mid) and to a lesser extent NK cells (FIG. 5c, right).

Lack of Autoimmunity in MUC1 Tg. Mice Reconstituted with scTCR-Transduced BM Cells. In order to test whether T cells expressing this TCR can develop normally in the presence of MUC1, we reconstituted C57BL6 wild type mice and mice transgenic for human MUC1 (MUC1 Tg.) with scTCR-transduced BM and six weeks later compared the percentages of scTCR-expressing cells. Table 1 shows that similar percentages of scTCR+ T cells as well as other immune cells were seen in C57BL/6 and MUC1 Tg. mice, showing that that there was no selection against the scTCR-expressing cells in MUC1 Tg. mice. Successful reconstitution of MUC1 Tg. mice allowed us also to determine if the expression of this receptor could have deleterious effects on normal tissues expressing MUC1, such as the lung and the pancreas.

TABLE I scTCR-expressing cells in reconstituted C57BL/6 and MUC1 Tg. mice

| Cell Type | | TCR Reconstituted | |
|---|---|---|---|
| (Surface Marker) | Control | C57BL/6 | MUC1 Tg. |
| T cells (CD3$^+$) | 0.2 ± 0$^C$ | 6.4 ± 1.3 | 9.0 ± 5.7 |
| B cells (B220$^+$) | 0.2 ± 0 | 9.7 ± 0.3 | 9.5 ± 1.6 |
| Granulocytes (GR-1$^+$) | 0.2 ± 0.7 | 30.8 ± 21.5 | 27.4 ± 9.2 |
| NK cells (DX5$^+$) | 0.1 ± 0 | 28.5 ± 4.3 | 18.5 ± 3.7 |
| Monocytes (F4/80$^+$) | 0.1 ± 0.2 | 20.4 ± 5.0 | 14.6 ± 2.7 |

Figure 6:
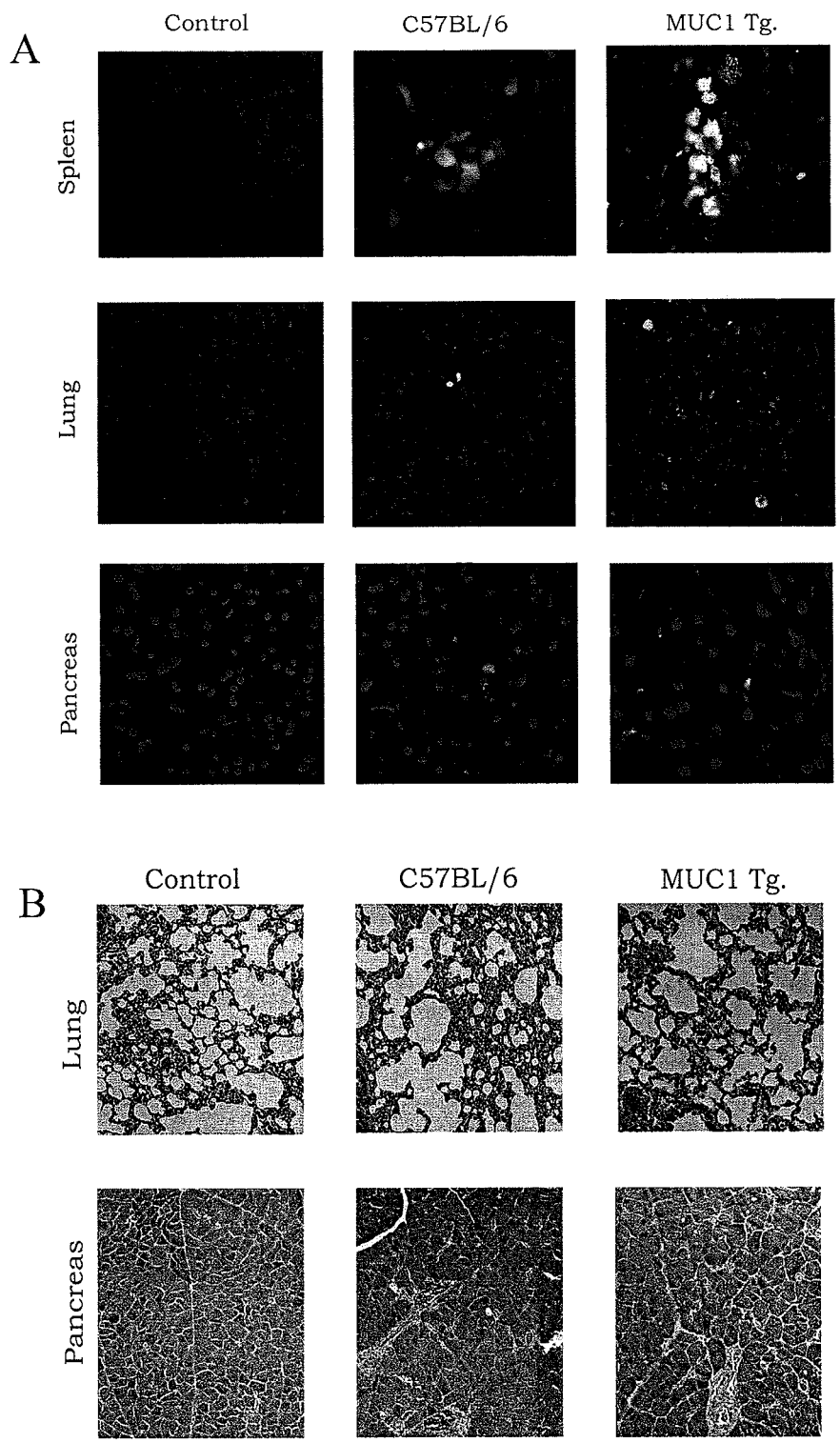
FIG. 6 shows expression of scTCR on immune cells has no deleterious effects on MUC1+ normal tissues.

The analysis was in Table 1 was performed six weeks post reconstitution with scTCR transduced BM. C57BL/6 refers to untreated mice. The numerical values in Table 1 refer to the mean %±the standard deviation. FIG. 6A shows very few EGFP+ cells infiltrating these tissue and no difference between wt and MUC1 Tg. mice. There was also no evidence of destruction of MUC1 expressing tissues in MUC1 Tg. Mice (FIG. 6B).

Figure 7:
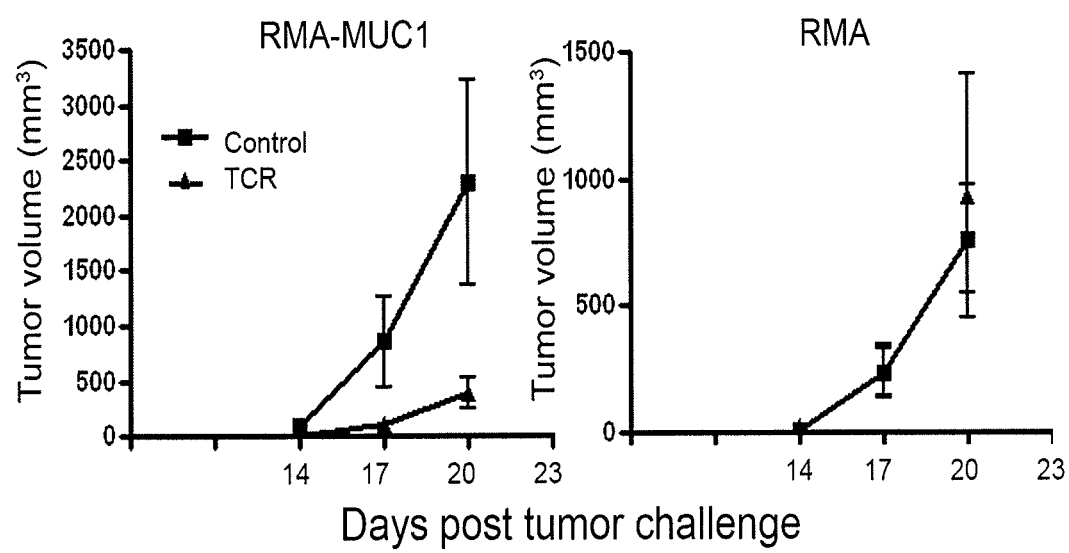
FIG. 7 shows scTCR-reconstituted MUC1 Tg. mice rejected MUC1+ tumor challenge. MUC1 Tg. mice were reconstituted with BM cells transduced with scTCR (filled triangle) or with control supernatant (filled square) and challenged 6 weeks later with MUC1$^-$ tumor (RMA) or with RMA cells transfected with MUC1 (RMA-MUC1). Data are presented as Mean±S.E. The number of mice at each time point ranged from 5-10.

One potential explanation for the lack of autoimmunity in reconstituted MUC1Tg mice could be that these cells are rendered tolerant or anergic in the presence of MUC1 as a self-antigen. This was not the case, however, since these mice successfully controlled the growth of a mouse tumor RMA transfected with human MUC1 (RMA-MUC) much better than the control mice. There was no inhibition of growth of the untransfected RMA control (FIG. 7).

This example shows that a suitable receptor of the invention (such as an MHC-unrestricted TCR specific for an epitope on the tumor antigen MUC1) expressed on cells of the innate and the adaptive immune system is able to direct the effector functions of these cells specifically against cancer cells displaying the MUC1 tumor antigen. The MHC-unrestricted nature of the TCR, combined with the stable expression of the MUC1 tumor antigen on a large number of human tumors (over 80%), makes therapy based on this TCR (scTCR) applicable to a large number of patients with a variety of tumors. Our experiments in SCID mice showed that the cells of the innate system alone can control tumor growth when provided with the tumor antigen-specific TCR. ScTCR expressing cells were seen as early as 3 weeks post-reconstitution and were still present at high numbers more than 7 months later. Both, the early presence of tumor-specific cells and their permanence would be expected to provide a beneficial anti-tumor effect. Furthermore, the persistence of scTCR+ cells (FIG. 9) suggests that among the many different cells that were transduced in the BM, there were also the long-term reconstituting hematopoietic stem cells that can continue to provide scTCR+ progenitors and mature cells throughout the life of the animal. Advantageously, expression of this TCR on large percentages of immune and other hematopoietic cells is not detrimental to the well-being of the animal. Long-term follow up (more than 12 months) of reconstituted mice transgenic for human MUC1 showed no signs of autoimmunity and no specific infiltration of cells into normal tissues that express MUC1. We hoped this would be the result because the epitope recognized by the sTCR has been shown to be expressed on the hypoglycosylated MUC1 made primarily by tumor cells.

The studies we describe here provide a reasonable expectation that this reagent is useful for immunotherapy of cancer. For example, a patient can be treated by transducing this scTCR into bone marrow or peripheral stem cells before infusing the cells into patients who have undergone high-dose chemotherapy (HDCT). HDCT followed by autologous stem cell or BM transplant, primarily performed in breast cancer patients, has had a limited, but positive, therapeutic success. The high rate of post-transplantation relapse in these patients could be a result of the survival of some tumor cells following HDCT treatment or could result from infusing contaminating tumor cells with the stem cell preparation. Vaccination trials aimed at augmenting the immune responses to eradicate residual tumor cells following stem cell therapy has shown minimal success, probably as a result of the poor and slow reconstitution of the T cell compartment in these patients. The recovery of the innate compartment of the immune system (in particular NK cells), however, occurs very rapidly after transplantation, reaching normal levels within a month post-transplantation. Accordingly, transducing BM cells with a MUC1-specific TCR or other receptor of the invention prior to transplantation will result in the expression of a tumor-specific receptor on a high percentage of quickly reconstituting cells of the innate immune system, which could promptly target and destroy residual tumor cells. Because MUC1 is expressed as a tumor antigen on greater than 80% of all human tumors, and the inventive receptor can direct effector cells to all such tumors in virtually all patients, there are few limits for its clinical application. By selecting a suitable expression vector, one can target various effector cells for in vitro or in vivo transduction and tailor this type of gene therapy or aimmunotherapy to specific stages of disease and combinations with other therapies.

The following references can be consulted to better understand the present invention and the foregoing example.

1. Slamon, D. J., B. Leyland-Jones, S. Shak, H. Fuchs, V. Paton, A. Bajamonde, A. Fleming, W. Eiermann, J. Wolter, M. Pegram, J. Baselga, and L. Norton. 2001. Use of chemotherapy plus a monoclonal antibody against HER2 for metastatic breast cancer that overexpresses HER2. *N Engl J Med* 344:783-792.
2. Davis, T. A., D. G. Maloney, D. K. Czerwinski, T. M. Liles, and R. Levy. 1998. Anti-idiotype antibodies can induce long-term complete remissions in non-Hodgkin's lymphoma without eradicating the malignant clone. *Blood* 92:1184-1190.
3. Yee, C., J. A. Thompson, D. Byrd, S. R. Riddell, P. Roche, E. Celis, and P. D. Greenberg. 2002. Adoptive T cell therapy using antigen-specific CD8+ T cell clones for the treatment of patients with metastatic melanoma: in vivo persistence, migration, and antitumor effect of transferred T cells. *Proc Natl Acad Sci USA* 99:16168-16173.
4. Fernandez, N. C., A. Lozier, C. Flament, P. Ricciardi-Castagnoli, D. Bellet, M. Suter, M. Perricaudet, T. Tursz, E. Maraskovsky, and L. Zitvogel. 1999. Dendritic cells directly trigger NK cell functions: cross-talk relevant in innate anti-tumor immune responses in vivo. *Nat Med* 5:405-411.
5. Saio, M., S. Radoja, M. Marino, and A. B. Frey. 2001. Tumor-infiltrating macrophages induce apoptosis in activated CD8(+) T cells by a mechanism requiring cell contact and mediated by both the cell-associated form of TNF and nitric oxide. *J Immunol* 167:5583-5593.
6. Diefenbach, A., E. R. Jensen, A. M. Jamieson, and D. H. Raulet. 2001. Rae1 and H60 ligands of the NKG2D receptor stimulate tumour immunity. *Nature* 413:165-171.
7. Medzhitov, R., and C. A. Janeway, Jr. 1997. Innate immunity: the virtues of a nonclonal system of recognition. *Cell* 91:295-298.
8. Pinthus, J. H., T. Waks, K. Kaufman-Francis, D. G. Schindler, A. Harmelin, H. Kanety, J. Ramon, and Z. Eshhar. 2003. Immuno-gene therapy of established prostate tumors using chimeric receptor-redirected human lymphocytes. *Cancer Res* 63:2470-2476.
9. Willemsen, R. A., R. Debets, P. Chames, and R. L. Bolhuis. 2003. Genetic engineering of T cell specificity for immunotherapy of cancer. *Hum Immunol* 64:56-68.
10. Adams, G. P., R. Schier, A. M. McCall, H. H. Simmons, E. M. Horak, R. K. Alpaugh, J. D. Marks, and L. M. Weiner. 2001. High affinity restricts the localization and tumor penetration of single-chain fv antibody molecules. *Cancer Res* 61:4750-4755.
11. Bubenik, J. 2003. Tumour MHC class I downregulation and immunotherapy (Review). *Oncol Rep* 10:2005-2008.20
12. Restifo, N. P., F. Esquivel, Y. Kawakami, J. W. Yewdell, J. J. Mule, S. A. Rosenberg, and J. R. Bennink. 1993. Identification of human cancers deficient in antigen processing. *J Exp Med* 177:265-272.
13. Stanislawski, T., R. H. Voss, C. Lotz, E. Sadovnikova, R. A. Willemsen, J. Kuball, T. Ruppert, R. L. Bolhuis, C. J. Melief, C. Huber, H. J. Stauss, and M. Theobald. 2001. Circumventing tolerance to a human MDM2-derived tumor antigen by TCR gene transfer. *Nat Immunol* 2:962-970.
14. Morgan, R. A., M. E. Dudley, Y. Y. Yu, Z. Zheng, P. F. Robbins, M. R. Theoret, J. R. Wunderlich, M. S. Hughes, N. P. Restifo, and S. A. Rosenberg. 2003. High efficiency TCR gene transfer into primary human lymphocytes affords avid recognition of melanoma tumor antigen glycoprotein 100 and does not alter the recognition of autologous melanoma antigens. *J Immunol* 171:3287-3295.
15. Magarian-Blander, J., P. Ciborowski, S. Hsia, S. C. Watkins, and O. J. Finn. 1998. Intercellular and intracellular events following the MHC-unrestricted TCR recognition of a tumor-specific peptide epitope on the epithelial antigen MUC1. *J Immunol* 160:3111-3120.

16. Fontenot, J. D., S. V. Mariappan, P. Catasti, N. Domenech, O. J. Finn, and G. Gupta. 1995. Structure of a tumor associated antigen containing a tandemly repeated immunodominant epitope. *J Biomol Struct Dyn* 13:245-260.
17. Fontenot, J. D., N. Tjandra, D. Bu, C. Ho, R. C. Montelaro, and O. J. Finn. 1993. Biophysical characterization of one-, two-, and three-tandem repeats of human mucin (muc-1) protein core. *Cancer Res* 53:5386-5394.
18. Jemal, A., T. Murray, A. Samuels, A. Ghafoor, E. Ward, and M. J. Thun. 2003. Cancer statistics, 2003. *CA Cancer J Clin* 53:5-26.
19. Altschul, S. F., W. Gish, W. Miller, E. W. Myers, and D. J. Lipman. 1990. Basic local alignment search tool. *J Mol Biol* 215:403-410.
20. Garcia, K. C., M. Degano, R. L. Stanfield, A. Brunmark, M. R. Jackson, P. A. Peterson, L. Teyton, and I. A. Wilson. 1996. An alphabeta T cell receptor structure at 2.5 A and its orientation in the TCR-MHC complex. *Science* 274:209-219.
21. Jones, T. A., J. Y. Zou, S. W. Cowan, and Kjeldgaard. 1991. Improved methods for building protein models in electron density maps and the location of errors in these models. *Acta Crystallogr A* 47 (Pt 2):110-119.
22. Schafineister, C. E. A. F., W. S. Ross, and V. Romanovski. 1995. LeAP. *University of California, San Francisco*.
23. Pearlman, D. A., D. A. Case, J. W. Caldwell, W. S. Ross, T. E. Cheatham, S. DeBolt, D. Ferguson, G. Seibel, and P. Kollman. 1995. AMBER, a package of computer programs for applying molecular mechanics, normal mode analysis, molecular dynamics and free energy calculations to simulate the structural and energetic properties of molecules. *Computer physics communications* 91:1-41.
24. Kraulis, P. J. 1991. MOLSCRIPT: A Program to Produce Both Detailed and Schematic Plots of Protein Structures. *Journal of Applied Crystallography* 24:946-950.
25. Merritt, E. A., and D. J. Bacon. 1997. Raster3D: Photorealistic Molecular Graphics. *Methods in Enzymology* 277:505-524.
26. Callan, M. F., H. T. Reyburn, P. Bowness, S. Rowland-Jones, J. I. Bell, and A. J. McMichael. 1995. Selection of T cell receptor variable gene-encoded amino acids 21 on the third binding site loop: a factor influencing variable chain selection in a T cell response. *Eur J Immunol* 25:1529-1534.
27. Vlad, A. M., S. Muller, M. Cudic, H. Paulsen, L. Otvos, Jr., F. G. Hanisch, and O. J. Finn. 2002. Complex carbohydrates are not removed during processing of glycoproteins by dendritic cells: processing of tumor antigen MUC1 glycopeptides for presentation to major histocompatibility complex class II-restricted T cells. *J Exp Med* 196:1435-1446.
28. Wang, G., R. K. Chopra, R. E. Royal, J. C. Yang, S. A. Rosenberg, and P. Hwu. 1998. A T cell-independent antitumor response in mice with bone marrow cells retrovirally transduced with an antibody/Fc-gamma chain chimeric receptor gene recognizing a human ovarian cancer antigen. *Nat Med* 4:168-172.
29. Ohashi, T., S. Boggs, P. Robbins, A. Bahnson, K. Patrene, F. S. Wei, J. F. Wei, J. Li, L. Lucht, Y. Fei, and et al. 1992. Efficient transfer and sustained high expression of the human glucocerebrosidase gene in mice and their functional macrophages following transplantation of bone marrow transduced by a retroviral vector. *Proc Natl Acad Sci USA* 89:11332-11336.
30. Burchell, J., J. Taylor-Papadimitriou, M. Boshell, S. Gendler, and T. Duhig. 1989. A short sequence, within the amino acid tandem repeat of a cancer-associated mucin, contains immunodominant epitopes. *Int J Cancer* 44:691-696.
31. Barnd, D. L., M. S. Lan, R. S. Metzgar, and O. J. Finn. 1989. Specific, major histocompatibility complex-unrestricted recognition of tumor-associated mucins by human cytotoxic T cells. *Proc Natl Acad Sci USA* 86:7159-7163.
32. Magarian-Blander, J., N. Domenech, and O. J. Finn. 1993. Specific and effective T-cell recognition of cells transfected with a truncated human mucin cDNA. *Ann N Y Acad Sci* 690:231-243.
33. Chung, S., K. W. Wucherpfennig, S. M. Friedman, D. A. Hafler, and J. L. Strominger. 1994. Functional three-domain single-chain T-cell receptors. *Proc Natl Acad Sci USA* 91:12654-12658.
34. Engel, I., T. H. Ottenhoff, and R. D. Klausner. 1992. High-efficiency expression and solubilization of functional T cell antigen receptor heterodimers. *Science* 256:1318-1321.
35. Sanderson, S., and N. Shastri. 1994. LacZ inducible, antigen/MHC-specific T cell hybrids. *Int Immunol* 6:369-376.
36. Hanenberg, H., X. L. Xiao, D. Dilloo, K. Hashino, I. Kato, and D. A. Williams. 1996. Colocalization of retrovirus and target cells on specific fibronectin fragments increases genetic transduction of mammalian cells. *Nat Med* 2:876-882.
37. Kondo, M., A. J. Wagers, M. G. Manz, S. S. Prohaska, D. C. Scherer, G. F. Beilhack, J. A. Shizuru, and I. L. Weissman. 2003. Biology of hematopoietic stem cells and progenitors: implications for clinical application. *Annu Rev Immunol* 21:759-806.
38. Klug, C. A., S. Cheshier, and I. L. Weissman. 2000. Inactivation of a GFP retrovirus occurs at multiple levels in long-term repopulating stem cells and their differentiated progeny. *Blood* 96:894-901.
39. Holmberg, L. A., T. Demirer, S. Rowley, C. D. Buckner, G. Goodman, R. Maziarz, J. Klarnet, N. Zuckerman, G. Harrer, R. McCloskey, R. Gersh, R. Goldberg, W. Nichols, A. Jacobs, P. Weiden, P. Montgomery, S. Rivkin, F. R. Appelbaum, and W. I. Bensinger. 1998. High-dose busulfan, melphalan and thiotepa followed by 22 autologous peripheral blood stem cell (PBSC) rescue in patients with advanced stage III/IV ovarian cancer. *Bone Marrow Transplant* 22:651-659.
40. Bensinger, W. I., K. S. Schiffman, L. Holmberg, F. R. Appelbaum, R. Maziarz, P. Montgomery, E. Ellis, S. Rivkin, P. Weiden, K. Lilleby, S. Rowley, S. Petersdorf, J. P. Klarnet, W. Nichols, A. Hertler, R. McCroskey, C. H. Weaver, and C. D. Buckner. 1997. High-dose busulfan, melphalan, thiotepa and peripheral blood stem cell infusion for the treatment of metastatic breast cancer. *Bone Marrow Transplant* 19:1183-1189.
41. Brenner, M. K., D. R. Rill, M. S. Holladay, H. E. Heslop, R. C. Moen, M. Buschle, R. A. Krance, V. M. Santana, W. F. Anderson, and J. N. Ihle. 1993. Gene marking to determine whether autologous marrow infusion restores long-term haemopoiesis in cancer patients. *Lancet* 342:1134-1137.
42. Holmberg, L. A., D. V. Oparin, T. Gooley, K. Lilleby, W. Bensinger, M. A. Reddish, G. D. MacLean, B. M. Longenecker, and B. M. Sandmaier. 2000. Clinical outcome of breast and ovarian cancer patients treated with high-dose chemotherapy, autologous stem cell rescue and THERATOPE STn-KLH cancer vaccine. *Bone Marrow Transplant* 25:1233-1241.

43. Avigan, D., Z. Wu, R. Joyce, A. Elias, P. Richardson, D. McDermott, J. Levine, L. Kennedy, N. Giallombardo, D. Hurley, J. Gong, and D. Kufe. 2000. Immune reconstitution following high-dose chemotherapy with stem cell rescue in patients with advanced breast cancer. *Bone Marrow Transplant* 26:169-176.

44. Koehne, G., W. Zeller, M. Stockschlaeder, and A. R. Zander. 1997. Phenotype of lymphocyte subsets after autologous peripheral blood stem cell transplantation. *Bone Marrow Transplant* 19:149-156.

encoded and expressed as a single molecule and does not require individual cells to be transduced by multiple nucleic acids. Moreover, this example describes a mammalian expression vector encoding a soluble human TCR. The approaches used in this example for manipulation of a human tumor specific TCR also can be used to study various aspects of TCR-based immunotherapy.

The following section of this example sets forth the MATERIALS AND METHODS used herein.

Primers. Sequences of the oligonucleotide primers (i.e., P1-P15) used for cloning are listed in Table 2, along with restriction enzyme cleavage and GenBank accession number.

TABLE 2

| Primer No. | Accession No. | Sequence |
|---|---|---|
| P1 | DQ269212 | 5'-CGGGATCCTCGAGATGGAGACCCTCTTGGGCCTGCTTA-3' (SEQ ID NO: 8) |
| P2 | DQ269213 | 5'-CGGGATCCGTCGACATGGCCACCAGGCTCCTCTGCTG-3' (SEQ ID NO: 9) |
| P3 | DQ269212 | 5'-CGGGATCCGGAATTCTCAGCTGGACCACAGCCGCAGCGT-3' (SEQ ID NO: 10) |
| P4 | DQ269213 | 5'-ATAGTTTAGCGGCCGCGGATCCTCAGAAATCCTTTCTCTTGACCA-3' (SEQ ID NO: 11) |
| P5 | J04132 | 5'-GGGGATCCCAAACTCTGCTACCTGCTGG-3' (SEQ ID NO: 12) |
| P6 | J04132 | 5'TCCCCGCGGCGGCCGCGAATTCTTAGCGAGGGGGCAGGGCCTGCATG-3' (SEQ ID NO: 13) |
| P7 | DQ269212 | 5'-CGGGATCCAGATCCCCACAGGAACTTTCTGGGCTGGGGAAG-3' (SEQ ID NO: 14) |
| P8 | DQ269213 | 5'-CGGGATCCAGATCCCCACAGTCTGCTCTACCCCAGGCCTCG-3' (SEQ ID NO: 15) |
| P9 | DQ269213 | 5'-AGGCGCGCCCCCAGGCCTCGGCGCTGACGATC-3' (SEQ ID NO: 16) |
| P10 | BT019811 | 5'-AGGCGCGCCGACATGGCCCTGATTGTGCTGGGGGGC-3' (SEQ ID NO: 17) |
| P11 | BT019811 | 5'-AGGCGCGCCGACGCTGGGGATATGGCCCTGATTGTGCTGGG-3' (SEQ ID NO: 18) |
| P12 | DQ269213 | 5'CTAAGCGTAGTCTGGGACGTCGTATGGGTACAGATCCTCTTCTGAGATGAGTTTTTGTTCTACAACGGTTAACCTGGTC-3' (SEQ ID NO: 19) |
| P13 | DQ269213 | 5'CCTGCAGGTCAATGGTGATGGTGATGATGCTTGTCATCGTCATCCTTGTAGTCAGCGTCTGCTCTACCCCAGG-3' (SEQ ID NO: 20) |
| P14 | DQ269212 | 5'ATGTGGCTGCAGAGCCTGCTGCTCTTGGGCACTGTGGCCTGCAGCATCTCTGCACCCCAGGAGGTGACGCAGATTC-3' (SEQ ID NO: 21) |
| P15 | DQ269212 | 5'CCATGGAGACAGACACACTCCTGCTATGGGTACTGCTGCTCTGGGTTCCAGGTTCCACTGGTGACGCGGCCCAGGAGGTGACGCAGATTC-3' (SEQ ID NO: 22) |

EXAMPLE 2

This example describes the design and construction of several gene transfer vectors for expression in mammalian cells of membrane bound and soluble human T cell receptors (TCR). In particular, this example describes a vector (TCR α-IRES-β pEF4) that encodes high-level expression of a full-length TCR of the present invention on the surface of T cells. Furthermore, this example describes a chimeric TCR that does not require the presence of endogenous CD3 molecules for surface expression, which allows the receptor to be expressed on cells other than T cells. This example also describes a vector encoding a single chain TCR (scTCR) as a fusion protein of VαVβCβ with CD3ζ. Advantageously, this scTCR is well suited for gene therapy because it is Cloning of Full-Length TCR α and β Chains. MA CTL clone, the source of the TCR, is described in Magarian-Blander et al. (*J. Immunol*, 160: 3111-3120 (1998)). RT-PCR was performed using GeneAmp RT-PCR kit (Applied Biosystems, Foster City, Calif. USA) and using either Vα (P1) or Vβ (P2) leader sequence specific forward primers and Cα (P3) or Cβ (P4) reverse primers. The TCR α and β chains were cloned into the multiple cloning site A (MCSA) and multiple cloning site B (MCSB) in the pIRES vector (Clontech Laboratories, Palo Alto, Calif., USA). The TCRα-IRES-TCRβ cassette was then subcloned into the pEF4 mammalian expression vector (Invitrogen, FIG. 10A).

Construction of a Two Chain TCR (tcTCR) and a Single Chain TCR (scTCR) Expression Vectors for Expression on T Cells and Non-T Cells. Human CD3 ζ chain was cloned using forward primer (P5) and reverse primer (P6). This cloning strategy maintained an endogenous BamH I site at nucleotide number 80 in the extracellular domain of human CD3 ζ. The PCR product was cloned into the pCDNA3.1 TA vector (Invitrogen). The extracellular domains of the TCR α and β chains were cloned using (P1) or (P2) forward primers and (P7) or (P8) reverse primers. The CD3 ζ/pCDNA3.1 vector was digested with BamH I restriction enzyme (New England BioLabs, Beverly, Mass., USA) and the TCR α or β chains were cloned in-frame with the CD3 ζ chain at the BamH I site (FIG. 11A and FIG. 11B). The TCR αζ and βζ were subcloned into the pIRES vector and finally the αζ-IRES-βζ cassette was subcloned into the pLNCX2 (Clontech) expression vector (FIG. 11C). The scTCR was constructed by cloning the TCR VαJα and joining into the TCR VβDβJβCβ region using flexible linker (GGGGS)$_3$. The TCR VαJα-VβDβJβCβ was then ligated in-frame to the murine CD3 ζ chain. A linker encoding a thrombin cleavage site, GDLVPRGSSRLD (SEQ ID NO: 7), was introduced between the TCR β constant and the CD3 ζ transmembrane domain. The scTCR was cloned into the pEF6 vector.

Construction of scTCR-CD4TM-hζ Mammalian Expression Vectors. The scTCR VαJα-VβDβJβCβ extracellular domain was amplified using Vα forward (P1) and Cβ reverse (P9) and cloned into the pEF6 vector. An Asc I site was introduced at the C-terminus in the TCR Cβ region. The human CD4 transmembrane (TM) domain fused to the human CD3 ζ cytoplasmic domain was amplified from the hCD4ζ vector (obtained from Dr. Margo R. Roberts, University of Virginia, VA, USA) using forward (P10) and reverse (P6) primers. Asc I and Sac II sites were introduced into the forward and reverse primers, respectively that allowed in-frame ligation to the scTCR extracellular domain. A modified version of this vector was created by inserting a three amino acid (AGD) linker between the TCR Cβ region and the CD4 TM domain. In the latter, PCR was done using (P6) and (P11) primers.

Surface Biotin Labeling and Thrombin Cleavage of scTCR. Surface biotin labeling and thrombin cleavage was performed using convention methods as described in Engel et al. (*Science* 256: 1318-1321 (1992)).

Construction of Secreted scTCRs. A soluble, single chain fraction variable domain (sscFV) encoding the TCR VαJαVβDβJβ or soluble scTCR (sscTCR) domain consisting of the TCR VαJαVβDβJβCβ was cloned into pCDNA3.1 vector by RT-PCR using (P1) and (P12) or (P2) and (P13) primers, respectively. Modified versions of the sscTCR vector were created by fusing the sscTCR to the GM-CSF, PCR was done using P14 and P13, or Ig-κ light chain leader sequences (PCR was done using P15 and P13).

Cell Transfection. Human embryonic kidney cells, HEK 293H, were transfected using lipofectamine 2000 (Invitrogen) according to manufacturer's instruction. Cells were analyzed for protein expression 48-72 hours post-transfection. Jurkat cells were electroporated using a BioRad Gene Pulser II (Bio-Rad Laboratories, Hercules, Calif., USA) at 960 μF and 200 V settings.

Stimulation with Superantigen. BWZ and BWZ-scTCR cells were stimulated with SEE (Toxin Technology, Sarasota, Fla.). Thirty-six hours later, IL-2 in culture supernatant was measured using murine IL-2 ELISA kit (BD Pharmingen, San Diego, Calif.) according to manufacturer's recommendations.

Purification of Soluble scTCR and Western Blotting. Transfected 293H cells were grown in DMEM-10. Seventy-two hours after replacing with fresh medium, culture medium was harvested and used for protein purification. Anti-HA, c-Myc, and 6-His antibodies were purchased from Santa Cruz Biotechnology, Santa Cruz, Calif., USA. Anti-Flag M2 antibody was purchased from Sigma. For constructs encoding c-Myc or HA tagged proteins, sscTCR was purified using Protein G Sepharose beads (Amersham Biosciences) coated with the appropriate anti-tag antibody. For vectors encoding 6-His tagged proteins, sscTCR was purified using Nickel-Agarose column (Qiagen) according to manufacturer's recommendations.

The following section sets forth the RESULTS obtained in this example.

Figure 10:
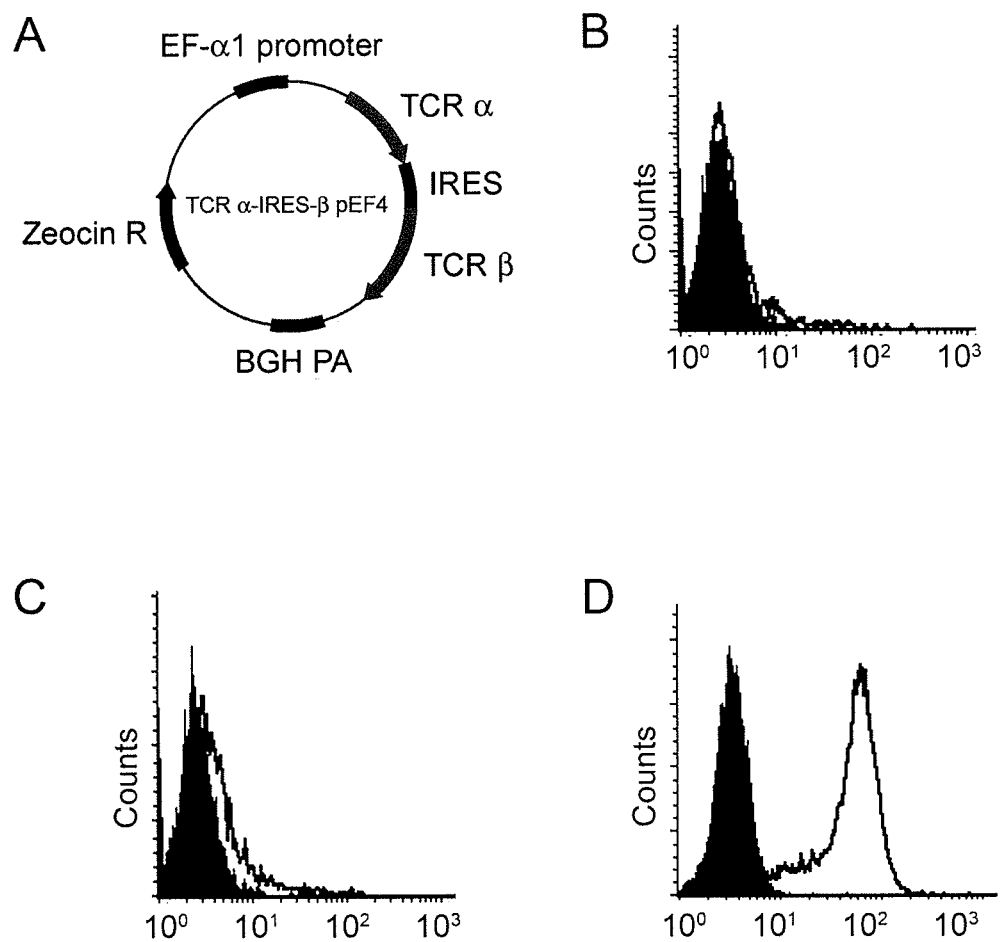
FIG. 10 shows expression of the TCR αβ from MA CTL clone on the surface of a TCR-deficient Jurkat line (JRT3-T3.5). The TCR α-IRES-β cassette was cloned into the pEF4 expression vector (FIG. 10A), Untransfected JRT3-T3.5 (FIG. 10B), JRT3-T3.5 cells transfected with the TCR β chain (FIG. 10C), or JRT3-T3.5 cells transfected with MA TCR α-IRES-β pEF4 (FIG. 10D), were stained with anti-CD3ε (open histogram) or with isotype control (filled histogram) antibody. IRES means internal ribosomal entry site, and Zeocin is an antibiotic resistance gene.

Reconstitution of the TCR/CD3 Complex on the Surface of JRT3-T3.5 Jurkat Line Transfected with the TCR α and β Chain Construct. J.RT3-T3.5 cells lack the TCR β transcript and have low levels of the TCR α chain message, and are therefore useful host cells for testing the expression of transfected TCR. The pEF4 mammalian expression vector was chosen because expression of cloned genes is driven by the human elongation factor-1 alpha (EF-1α) promoter, which is expected to be more transcriptionally active and stable in T cells than viral promoters. In addition, the presence of the IRES sequence permits expression of the TCR α and β chain genes from the same message. This is expected to result in similar levels of expression of both genes, in contrast to genes driven by different promoters. As shown in FIG. 10, untransfected JRT3-T3.5 did not express the TCR/CD3 complex on their surface (FIG. 10A). Transfection of the TCR β chain alone didn't reconstitute the TCR/CD3 complex on cell surface (FIG. 10B); however, stable transfection of the TCRα-IRES-β pEF4 vector into J.RT3-T3.5 cells resulted in high levels of TCR/CD3 complex surface expression (FIG. 10C). Cells transfected with the TR-ALPHA-IRES-TR-BETA pEF4 vector recognized MUC1+ tumors in vitro.

Figure 11:
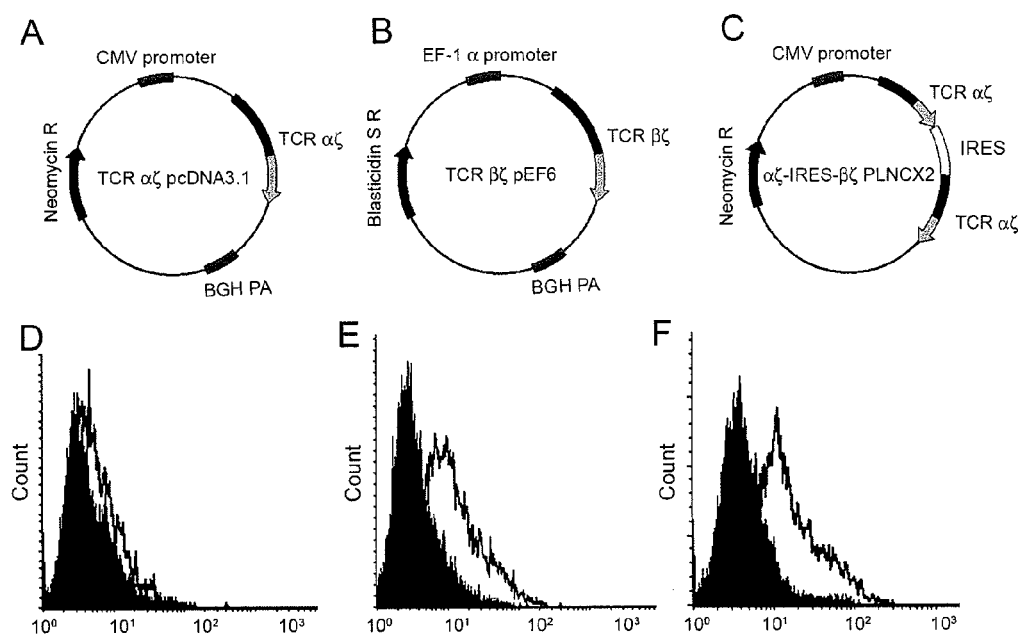
FIG. 11 shows the construction and expression of MUC1-specific αζ and βζ chimeric T cell receptors. Expression vectors for TCR αζ (FIG. 11A), βζ (FIG. 11B), and αζ/βζ (FIG. 11C). Untransfected 293H cells (FIG. 11D), 293H cells co-transfected with the TCR αζ and TCR βζ (FIG. 11E) or cells transfected with the αζ-IRES-βζ pLNCX2 (FIG. 11F) were stained for surface expression of the TCR using anti-TCR antibody βF1 (open histogram) or isotype control antibody (filled histogram).

Engineered MUC1-specific Two Chain TCRs (tcTCR) allows Expression on the Surface of Non-T Cells. The requirement for CD3 molecules for expression of the TCR on the cell surface limits its expression to T cells. Engineered vectors that would bypass this requirement were constructed and allow expression of TCRs and TCR like receptors on other cell types (Engel et al., *Science* 256: 1318-1321 (1992)). In T cells, the engineered vector eliminates the possibility that the transferred TCRs could pair with endogenous TCR α or β chains that could reduce the level of the specific receptor on the surface as well as form a potentially autoreactive TCR. Construction of the TCR αζ and βζ was done as detailed in the Materials and Methods. As shown in FIG. 11, transfection of the TCR αζ(A) and TCR βζ(B) constructs into human epithelial kidney HEK 293H (non-T cell) cells resulted in surface expression of the TCR α/β heterodimer (D and E). Similar levels of surface expression were also obtained when 293H cells were transfected with the TCR αζ-IRES-βζ pLNCX2 vector (FIGS. 11C and 11F).

Figure 12:
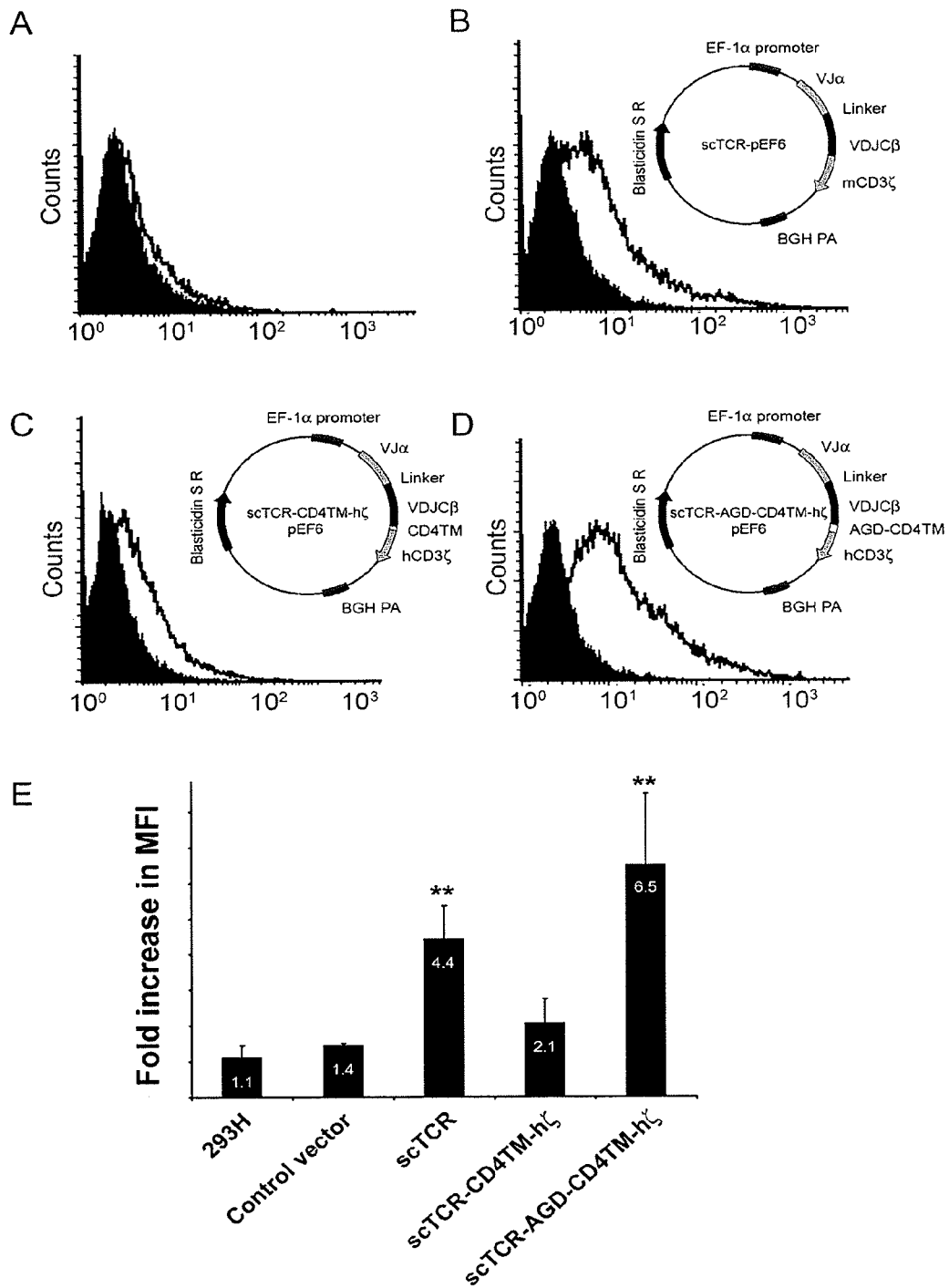
FIG. 12 shows vector construction and expression of MUC1-specific single chain T cell receptors (scTCRs). 293H cells (FIG. 12A) were transfected with the scTCR (FIG. 12B), scTCR-CD4TM-hζ (FIG. 12C), or scTCR-CD4TM-AGD-hζ (FIG. 12D) mammalian expression vectors. Cells were stained with anti-TCR βF1 (open histogram) or isotype control (filled histogram) antibody.
Figure 13:
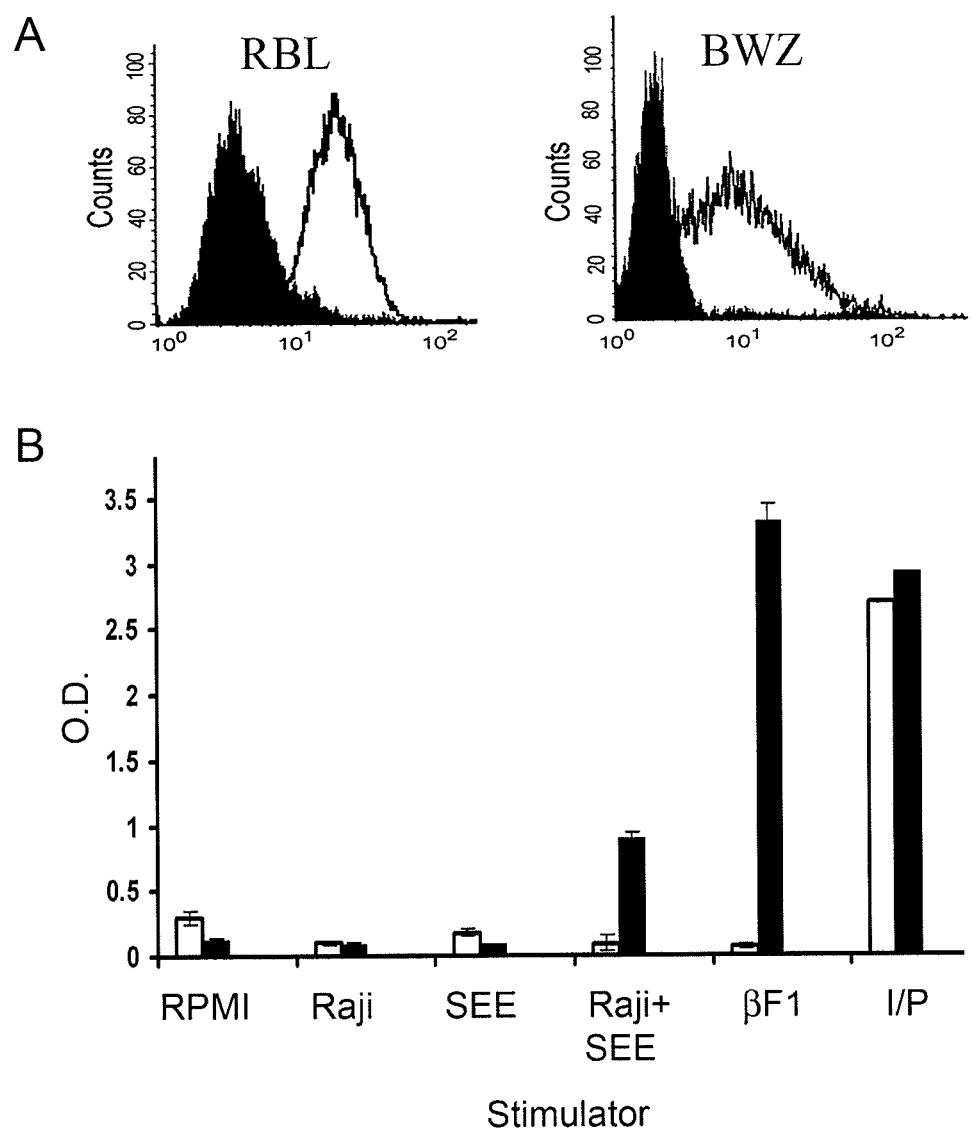
FIG. 13 shows expression of functional scTCR on the surface of T cells and non-T immune cells.

Different Configurations of Single Chain TCRs (scTCRs) were Expressed at Various Levels on the Surface of 293H Cells. For clinical application, transfection with multiple plasmids can be disadvantageous. Single chain (sc)TCR and single chain antibodies obviate this hurdle and are known in the art. We made three different MUC1 tumor antigen specific scTCR constructs and compared the levels of their surface expression (FIG. 12). FIG. 12 depicts the level of surface expression of scTCR (FIG. 12B), scTCR-CD4TM-hζ (FIG. 12C) and the scTCR-AGD-CD4TM-hζ (FIG. 12D). These scTCRs consist of the TCR antigen binding domain and a signaling component from the CD3 ζ chain. As shown in FIG. 3B, transfection of the scTCR into 293H cells resulted in a substantial increase in surface expression compared to control (A), and transfection with the scTCR-CD4TM-hζ construct gave a much lower level of expression (FIG. 3C). However, inserting a 3 amino acids (AGD) linker between the TCR Cβ chain and the CD4 TM domain restored high level of surface expression of the scTCR (FIG. 3D). While not desiring to be bound by any particular theory, it is possible that these 3 amino acids provided enough flexibility to the scTCR to allow proper folding of the molecule and normal level of surface expression. FIG. 12E shows the same results in a more quantitative way. High surface expression of the scTCR was detected on both T cells (BWZ murine thymoma) and non-T cells (RBL rat basophilic leukemia) transfected with TCR-pEF6 vector (FIG. 13A). The TCR is functional as shown by the ability of the transfected BWZ cells to be stimulated with plate-bound anti-TCR βF1 antibody or with SEE superantigen, which binds specifically to the human TCR Vβ8 region (FIG. 13B). These cells also recognized MUC1+ tumor cells in vitro (see Example 1).

Figure 14:
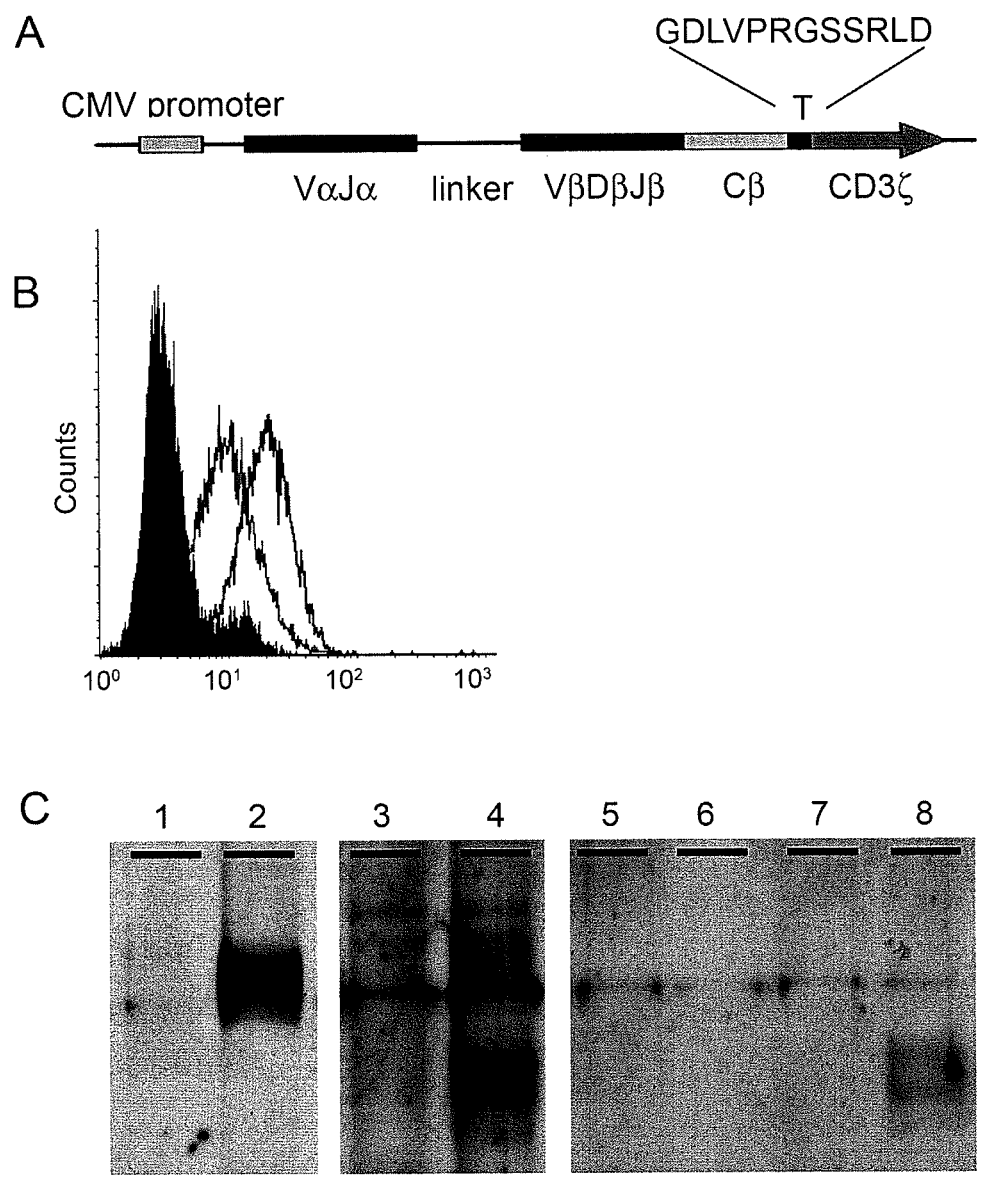
FIG. 14 shows expression and purification of soluble scTCR (sscTCR) following surface biotin labeling and immmunoprecipitation.

Multiple Expression Vectors for Soluble scTCR Production. Soluble single chain T cell receptors (sscTCRs) can be used as vehicles to deliver and target therapeutic drugs to the site of their specific antigen (e.g., a tumor expressing MUC1 tumor antigen). Additionally, sscTCR can be used to study the affinity of interaction between the TCR and its ligand using, e.g., by Biacore analysis. We successfully generated sscTCR by inserting a thrombin cleavage site between the scTCR Cβ region and the CD3 ζ transmembrane domain (FIG. 14A). FIG. 14B shows that the scTCR containing the thrombin cleavage site can be cleaved from the surface of transfected cells. Following thrombin cleavage, the scTCR could be purified from the soluble fraction (FIG. 14C, lane 4) using an affinity column. As expected, the sscTCR has a lower molecular weight than the membrane bound scTCR (FIG. 14C, lanes 2 and 4). The sscTCR can be eluted from the affinity column under high pH elution conditions (FIG. 14C, lane 8). Even though this approach was successful in generating sscTCR, the amount that was obtained was extremely low. Other groups have reported expression of a soluble, single chain fraction variable (sscFV) domain of both antibody and T cell receptor. FIG. 15a shows the design of the sscFV construct that encodes the TCR VαJα-VβDβJP. FIG. 15b shows the same sscTCR construct that was terminated just before the last cystine in the TCR Cβ region. Two other constructs were designed as described in FIG. 15b, with the exception of replacing the Vα leader sequence in the sscTCR with either a GM-CSF (FIG. 15c) or Ig-k light chain (FIG. 15d) signal peptide. Various epitope tags were inserted at the C terminus to facilitate protein expression and purification. When the sscFV construct was transfected into 293H cells, no recombinant sscFV protein could be detected in the culture supernatant (FIG. 15e, lane a'). However, transfection of the sscTCR construct into 293H cells resulted in significant amounts of recombinant protein secreted in culture supernatants (FIG. 15e, lane b'). Transfection of the sscTCR that was fused to the Ig-κ light chain leader sequence gave a lower level of protein expression than was seen in b' (FIG. 15e, lane d'), and transfection of the sscTCR construct fused to the GM-CSF leader sequence yielded no protein secretion (FIG. 15e, lane c'). These results showed that the presence of the TCR β chain constant region is absolutely required for expression of the sscTCR. While not desiring to be bound by any particular theory, we hypothesized that the TCR β chain constant region must be important for the proper folding of the protein or that it interacts with and masks other hydrophobic amino acid residues in the TCR β chain VDJ region, otherwise the scFV is rendered insoluble. As shown in FIG. 15f, the recombinant sscTCR could be purified from culture supernatant using a nickel column. FIG. 15g shows the western blot analysis of purified fractions obtained in FIG. 15f, using anti-FLAG M2 antibody. The expression of soluble form scTCR in these mammalian cells appears to be sufficiently robust to produce this reagent for therapeutic purposes or for biophysical analyses.

Thus this example describes several mammalian expression vectors useful for functional high-level expression of human TCR α and β chains that are useful for biological and biochemical analyses, as well as immunotherapy. Our TCR α-IRES-β pEF4 vector encoding the tumor antigen-specific TCR generated high levels and stable expression of the TCR αβ/CD3 complex on the surface of transfected T cells. We also constructed chimeric TCR αζ and TCR βζ that were successfully expressed on the surface of 293H cells (a non T cell line that doesn't express the CD3 complex). Additionally, we showed that surface expression of the TCR was dependent on the co-expression of the TCR αζ and TCR βζ. We hypothesized that pairing of the TCR αζ to the TCR βζ was crucial for proper folding and transport of the heterodimer through the endoplasmic reticulum (ER) and Golgi and eventually to the cell surface.

In contrast to the expression of two chain TCRs, functional scTCRs can be expressed on the cell surface from a single mRNA transcript. In the example shown here we constructed a single chain TCR specific for the tumor antigen MUC1 and expressed it on the surface of different cell types. The expression of the scTCR on the surface of transfected cells was lower than the level of expression of the native TCR, which we attributed to the presence of charged amino acids in the transmembrane (TM) domain of the CD3 zeta chain that might cause dimerization and retention of the scTCR in the endoplasmic reticulum. In an attempt to increase the level of surface expression of the scTCR, we replaced the TM domain of CD3ζ in the scTCR with the TM domain of human CD4. However, this new construct was expressed at very low level until we inserted a 3 amino acid (AGD) linker between the scTCR constant region and the CD4 TM domain. High level of surface expression of the scTCR was restored in this new construct. The short linker provided either flexibility or sufficient spacing between the TCR constant region and CD4 TM to allow normal surface expression.

Most previous attempts to generate soluble TCR were made using prokaryotic expression systems. However, proteins expressed in prokaryotic cells lack post-translational modifications and may be improperly folded. In order to avoid these potential problems, we chose to express soluble MUC1-specific scTCR using mammalian expression systems. We terminated the scTCR construct just before the last cystine in the TCR□ constant region. Following transfection into 293H cells, large amount of soluble scTCR was detected in culture supernatants.

In conclusion the various constructs we adapted and tested for the expression of the MUC1-specific TCR can be of interest and help to other investigators interested in TCR immunotherapy or in studying TCR-antigen interactions.

The following references are useful in understanding the invention, and in particular this example:
1. Dudley M E, Wunderlich J R, Robbins P F, Yang J C, Hwu P, Schwartzentruber D J, Topalian S L, Sherry R, Restifo N P, Hubicki A M et al: Cancer regression and autoimmunity in patients after clonal repopulation with antitumor lymphocytes. *Science* 2002, 298(5594):850-854.

2. Rubinstein M P, Kadima A N, Salem M L, Nguyen C L, Gillanders W E, Nishimura M I, Cole D J: Transfer of TCR genes into mature T cells is accompanied by the maintenance of parental T cell avidity. *J Immunol* 2003, 170(3):1209-1217.
3. Morgan R A, Dudley M E, Yu Y Y, Zheng Z, Robbins P F, Theoret M R, Wunderlich J R, Hughes M S, Restifo N P, Rosenberg S A: High efficiency TCR gene transfer into primary human lymphocytes affords avid recognition of melanoma tumor antigen glycoprotein 100 and does not alter the recognition of autologous melanoma antigens. *J Immunol* 2003, 171(6):3287-3295.
4. Aarnoudse C A, Kruse M, Konopitzky R, Brouwenstijn N, Schrier P I: TCR reconstitution in Jurkat reporter cells facilitates the identification of novel tumor antigens by cDNA expression cloning. *Int J Cancer* 2002, 99(1):7-13.
5. Derby M A, Wang J, Margulies D H, Berzofsky J A: Two intermediate-avidity cytotoxic T lymphocyte clones with a disparity between functional avidity and MHC tetramer staining. *Int Immunol* 2001, 13(6):817-824.
6. Snyder J T, Alexander-Miller M A, Berzofskyl J A, Belyakov I M: Molecular mechanisms and biological significance of CTL avidity. *Curr HIV Res* 2003, 1(3): 287-294.
7. Weijtens M E, Hart E H, Bolhuis R L: Functional balance between T cell chimeric receptor density and tumor associated antigen density: CTL mediated cytolysis and lymphokine production. *Gene Ther* 2000, 7(1):35-42.
8. Yang S, Linette G P, Longerich S, Haluska F G: Anti-melanoma activity of CTL generated from peripheral blood mononuclear cells after stimulation with autologous dendritic cells pulsed with melanoma gp100 peptide G209-2M is correlated to TCR avidity. *J Immunol* 2002, 169(1):531-539.
9. Magarian-Blander J, Ciborowski P, Hsia S, Watkins S C, Finn O J: Intercellular and intracellular events following the MHC-unrestricted TCR recognition of a tumor-specific peptide epitope on the epithelial antigen MUC1. *J Immunol* 1998, 160(7):3111-3120.
10. Engel I, Ottenhoff T H, Klausner R D: High-efficiency expression and solubilization of functional T cell antigen receptor heterodimers. *Science* 1992, 256(5061):1318-1321.
11. Mittelbrunn M, Yanez-Mo M, Sancho D, Ursa A, Sanchez-Madrid F: Cutting edge: dynamic redistribution of tetraspanin CD81 at the central zone of the immune synapse in both T lymphocytes and APC. *J Immunol* 2002, 169(12):6691-6695.
12. Willemsen R A, Weijtens M E, Ronteltap C, Eshhar Z, Gratama J W, Chames P, Bolhuis R L: Grafting primary human T lymphocytes with cancer-specific chimeric single chain and two chain TCR. *Gene Ther* 2000, 7(16): 1369-1377.
13. Novotny J, Ganju R K, Smiley S T, Hussey R E, Luther M A, Recny M A, Siliciano R F, Reinherz E L: A soluble, single-chain T-cell receptor fragment endowed with antigen-combining properties. *Proc Natl Acad Sci USA* 1991, 88(19):8646-8650.
14. Eshhar Z, Bach N, Fitzer-Attas C J, Gross G, Lustgarten J, Waks T, Schindler D G: The T-body approach: potential for cancer immunotherapy. *Springer Semin Immunopathol* 1996, 18(2):199-209.
15. Gregoire C, Lin S Y, Mazza G, Rebai N, Luescher I F, Malissen B: Covalent assembly of a soluble T cell receptor-peptide-major histocompatibility class I complex. *Proc Natl Acad Sci USA* 1996, 93(14):7184-7189.
16. Pavlinkova G, Colcher D, Booth B J, Goel A, Batra S K: Pharmacokinetics and biodistribution of a light-chain-shuffled CC49 single-chain Fv antibody construct. *Cancer Immunol Immunother* 2000, 49(4-5):267-275.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated nucleic acid encoding a receptor, other than an immunoglobulin, wherein the receptor binds to a MUC1 tumor antigen independently of a major histocompatibility complex (MHC), wherein the receptor is an scFv and
   a. comprises a first amino acid sequence that is identical with the portion of MA Vα23 shown in FIG. 1 (SEQ ID NO:1) and
   b. comprises a second amino acid sequence that is identical with the portion of MA Vβ8.3 shown in FIG. 1 (SEQ ID NO:2).

2. The isolated nucleic acid of claim 1, wherein the receptor binds to MUC1 tumor antigen with about the same affinity for MUC1 as the MA TCR.

3. The isolated nucleic acid of claim 1, wherein the receptor binds to MUC1 tumor antigen with a higher affinity for MUC1 as the MA TCR.

4. The isolated nucleic acid of claim 1, wherein the receptor binds to MUC1 tumor antigen with a lower affinity for MUC1 as the MA TCR.

5. The isolated nucleic acid of claim 1, wherein the receptor is a single chain receptor.

6. The isolated nucleic acid of claim 1, wherein the receptor comprises an amino acid sequence comprising a first portion and a second portion and further comprising a linker of from 1 to about 30 amino acids between the first portion of the amino acid sequence and the second portion of the amino acid sequence.

7. The isolated nucleic acid of claim 1, wherein the receptor is expressed in a T cell better than an otherwise identical receptor lacking the linker in an identical T cell.

8. The isolated nucleic acid of claim 6, wherein the linker improves the expression of the receptor in a cell in comparison to an otherwise identical receptor lacking the linker.

9. The isolated nucleic acid of claim 6, wherein the linker does not have a function selected from the group consisting of an immunological function, a membrane spanning function, a signaling function, and a dimerization function.

10. The isolated nucleic acid of claim 1, wherein the Kd of the receptor for a single MUC1 epitope is between 0.2 μM and 200 μM.

11. The isolated nucleic acid of claim 6, wherein the receptor comprises a portion of the zeta-chain of CD3.

12. The isolated nucleic acid of claim 11, wherein the portion of the zeta-chain comprises the transmembrane spanning region of CD3.

13. The isolated nucleic acid of claim 1, wherein the receptor comprises a portion of the zeta-chain of CD3.

14. The isolated nucleic acid of claim 13, wherein the portion of the zeta-chain comprises the transmembrane spanning region of CD3.

* * * * *

SEQUENCE LISTING

```
<160> NUMBER OF SEQ ID NOS: 24

<210> SEQ ID NO 1
<211> LENGTH: 110
<212> TYPE: PRT
<213> ORGANISM: Artificial
<220> FEATURE:
```

<223> OTHER INFORMATION: MA V-alpha 23

<400> SEQUENCE: 1

Gln Glu Val Thr Gln Ile Pro Ala Ala Leu Ser Val Pro Glu Gly Glu
1               5                   10                  15

Asn Leu Val Leu Asn Cys Ser Phe Thr Asp Ser Ala Ile Tyr Asn Leu
            20                  25                  30

Gln Trp Phe Arg Gln Asp Pro Gly Lys Gly Leu Thr Ser Leu Leu Leu
        35                  40                  45

Ile Gln Ser Ser Gln Arg Glu Gln Thr Ser Gly Arg Leu Asn Ala Ser
50                  55                  60

Leu Asp Lys Ser Ser Gly Arg Thr Thr Leu Tyr Ile Ala Ala Ser Gln
65                  70                  75                  80

Pro Gly Asp Ser Ala Thr Tyr Leu Cys Ala Val Thr Ser Ser Tyr Gly
                85                  90                  95

Lys Leu Thr Phe Gly Gln Gly Thr Ile Leu Thr Val His Pro
            100                 105                 110

<210> SEQ ID NO 2
<211> LENGTH: 112
<212> TYPE: PRT
<213> ORGANISM: Artificial
<220> FEATURE:
<223> OTHER INFORMATION: MA V-beta 8.3

<400> SEQUENCE: 2

Asp Ala Arg Val Thr Gly Thr Pro Arg His Lys Val Thr Glu Met Gly
1               5                   10                  15

Gln Glu Val Thr Met Arg Cys Gln Pro Ile Leu Gly His Asn Thr Val
            20                  25                  30

Phe Trp Tyr Arg Gln Thr Met Met Gln Gly Leu Glu Leu Leu Gln Tyr
        35                  40                  45

Phe Arg Asn Arg Ala Pro Leu Asp Asp Ser Gly Met Pro Lys Asp Arg
    50                  55                  60

Phe Ser Ala Glu Met Pro Asp Ala Thr Leu Ala Thr Leu Lys Ile Gln
65                  70                  75                  80

Pro Ser Glu Pro Arg Asp Ser Ala Val Tyr Phe Cys Ala Ser Gly Leu
                85                  90                  95

Gly Glu Ala Ser Gly Tyr Thr Phe Gly Ser Gly Thr Arg Leu Thr Val
            100                 105                 110

<210> SEQ ID NO 3
<211> LENGTH: 5
<212> TYPE: PRT
<213> ORGANISM: Artificial
<220> FEATURE:
<223> OTHER INFORMATION: Muc-1 epitope

<400> SEQUENCE: 3

Pro Asp Thr Arg Pro
1               5

<210> SEQ ID NO 4
<211> LENGTH: 15
<212> TYPE: PRT
<213> ORGANISM: Artificial
<220> FEATURE:
<223> OTHER INFORMATION: linker

<400> SEQUENCE: 4

```
Gly Gly Gly Gly Ser Gly Gly Gly Ser Gly Gly Gly Ser
1               5                   10                  15
```

<210> SEQ ID NO 5
<211> LENGTH: 12
<212> TYPE: PRT
<213> ORGANISM: Artificial
<220> FEATURE:
<223> OTHER INFORMATION: linker

<400> SEQUENCE: 5

```
Gly Asp Leu Val Pro Arg Gly Ser Ser Arg Leu Asp
1               5                   10
```

<210> SEQ ID NO 6
<211> LENGTH: 20
<212> TYPE: PRT
<213> ORGANISM: Artificial
<220> FEATURE:
<223> OTHER INFORMATION: repeat unit of 140mer synthetic MUC1 peptide

<400> SEQUENCE: 6

```
Pro Asp Thr Arg Pro Ala Pro Gly Ser Thr Ala Pro Pro Ala His Gly
1               5                   10                  15

Val Thr Ser Ala
            20
```

<210> SEQ ID NO 7
<211> LENGTH: 12
<212> TYPE: PRT
<213> ORGANISM: Artificial
<220> FEATURE:
<223> OTHER INFORMATION: thrombin cleavage site

<400> SEQUENCE: 7

```
Gly Asp Leu Val Pro Arg Gly Ser Ser Arg Leu Asp
1               5                   10
```

<210> SEQ ID NO 8
<211> LENGTH: 38
<212> TYPE: DNA
<213> ORGANISM: Artificial
<220> FEATURE:
<223> OTHER INFORMATION: primer

<400> SEQUENCE: 8
cgggatcctc gagatggaga ccctcttggg cctgctta                             38

<210> SEQ ID NO 9
<211> LENGTH: 37
<212> TYPE: DNA
<213> ORGANISM: Artificial
<220> FEATURE:
<223> OTHER INFORMATION: primer

<400> SEQUENCE: 9
cgggatccgt cgacatggcc accaggctcc tctgctg                              37

<210> SEQ ID NO 10
<211> LENGTH: 39
<212> TYPE: DNA
<213> ORGANISM: Artificial
<220> FEATURE:
<223> OTHER INFORMATION: primer

<400> SEQUENCE: 10
cgggatccgg aattctcagc tggaccacag ccgcagcgt           39

<210> SEQ ID NO 11
<211> LENGTH: 45
<212> TYPE: DNA
<213> ORGANISM: Artificial
<220> FEATURE:
<223> OTHER INFORMATION: primer

<400> SEQUENCE: 11
atagtttagc ggccgcggat cctcagaaat cctttctctt gacca    45

<210> SEQ ID NO 12
<211> LENGTH: 28
<212> TYPE: DNA
<213> ORGANISM: Artificial
<220> FEATURE:
<223> OTHER INFORMATION: primer

<400> SEQUENCE: 12
gggatcccca aactctgcta cctgctgg                       28

<210> SEQ ID NO 13
<211> LENGTH: 47
<212> TYPE: DNA
<213> ORGANISM: Artificial
<220> FEATURE:
<223> OTHER INFORMATION: primer

<400> SEQUENCE: 13
tccccgcggc ggccgcgaat tcttagcgag ggggcagggc ctgcatg  47

<210> SEQ ID NO 14
<211> LENGTH: 41
<212> TYPE: DNA
<213> ORGANISM: Artificial
<220> FEATURE:
<223> OTHER INFORMATION: primer

<400> SEQUENCE: 14
cgggatccag atccccacag gaactttctg ggctggggaa g        41

<210> SEQ ID NO 15
<211> LENGTH: 41
<212> TYPE: DNA
<213> ORGANISM: Artificial
<220> FEATURE:
<223> OTHER INFORMATION: primer

<400> SEQUENCE: 15
cgggatccag atccccacag tctgctctac cccaggcctc g        41

<210> SEQ ID NO 16
<211> LENGTH: 32
<212> TYPE: DNA
<213> ORGANISM: Artificial
<220> FEATURE:
<223> OTHER INFORMATION: primer

<400> SEQUENCE: 16
aggcgcgccc ccaggcctcg gcgctgacga tc                  32

<210> SEQ ID NO 17
<211> LENGTH: 36
<212> TYPE: DNA
<213> ORGANISM: Artificial

-continued

```
<220> FEATURE:
<223> OTHER INFORMATION: primer

<400> SEQUENCE: 17
aggcgcgccg acatggccct gattgtgctg gggggc                            36

<210> SEQ ID NO 18
<211> LENGTH: 41
<212> TYPE: DNA
<213> ORGANISM: Artificial
<220> FEATURE:
<223> OTHER INFORMATION: primer

<400> SEQUENCE: 18
aggcgcgccg acgctgggga tatggccctg attgtgctgg g                      41

<210> SEQ ID NO 19
<211> LENGTH: 79
<212> TYPE: DNA
<213> ORGANISM: Artificial
<220> FEATURE:
<223> OTHER INFORMATION: primer

<400> SEQUENCE: 19
ctaagcgtag tctgggacgt cgtatgggta cagatcctct tctgagatga gttttgttc   60 tacaacggtt aacctggtc                                               79

<210> SEQ ID NO 20
<211> LENGTH: 73
<212> TYPE: DNA
<213> ORGANISM: Artificial
<220> FEATURE:
<223> OTHER INFORMATION: primer

<400> SEQUENCE: 20
cctgcaggtc aatggtgatg gtgatgatgc ttgtcatcgt catccttgta gtcagcgtct  60
gctctacccc agg                                                    73

<210> SEQ ID NO 21
<211> LENGTH: 76
<212> TYPE: DNA
<213> ORGANISM: Artificial
<220> FEATURE:
<223> OTHER INFORMATION: primer

<400> SEQUENCE: 21
atgtggctgc agagcctgct gctcttgggc actgtggcct gcagcatctc tgcacccag   60 gaggtgacgc agattc                                                 76

<210> SEQ ID NO 22
<211> LENGTH: 90
<212> TYPE: DNA
<213> ORGANISM: Artificial
<220> FEATURE:
<223> OTHER INFORMATION: primer

<400> SEQUENCE: 22
ccatggagac agacacactc ctgctatggg tactgctgct ctgggttcca ggttccactg  60
gtgacgcggc ccaggaggtg acgcagattc                                  90

<210> SEQ ID NO 23
<211> LENGTH: 110
<212> TYPE: PRT
```

```
<213> ORGANISM: Artificial
<220> FEATURE:
<223> OTHER INFORMATION: SM3L

<400> SEQUENCE: 23

Asp Ile Val Val Thr Gly Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly
                100                 105                 110

<210> SEQ ID NO 24
<211> LENGTH: 110
<212> TYPE: PRT
<213> ORGANISM: Artificial
<220> FEATURE:
<223> OTHER INFORMATION: SM3H

<400> SEQUENCE: 24

Gln Glu Ser Gly Gly Gly Leu Val Gln Pro Gly Ser Met Lys Leu Ser
1               5                   10                  15

Cys Val Ala Ser Gly Phe Thr Phe Ser Asn Tyr Trp Met Asn Trp Val
            20                  25                  30

Arg Gln Ser Pro Glu Lys Gly Leu Glu Trp Val Ala Glu Ile Arg Leu
        35                  40                  45

Lys Ser Asn Asn Tyr Ala Thr His Tyr Ala Glu Ser Val Lys Gly Arg
    50                  55                  60

Phe Thr Ile Ser Arg Asp Asp Ser Lys Ser Ser Val Tyr Leu Gln Met
65                  70                  75                  80

Asn Asn Leu Arg Ala Glu Asp Thr Gly Ile Tyr Tyr Cys Thr Gly Val
                85                  90                  95

Gly Gln Phe Ala Tyr Trp Gly Gln Gly Thr Thr Val Thr Val
                100                 105                 110
```